US007110584B2

(12) United States Patent
Onami et al.

(10) Patent No.: US 7,110,584 B2
(45) Date of Patent: Sep. 19, 2006

(54) CELL LINEAGE EXTRACTING METHOD

(75) Inventors: Shuichi Onami, Setagaya-ku (JP); Shugo Hamahashi, Koto-ku (JP); Satoru Miyano, Nakano-ku (JP); Hiroaki Kitano, Kawagoe (JP)

(73) Assignee: Japan Science and Technology Corporation, Saitama (JP)

( * ) Notice: Subject to any disclaimer, the term of this patent is extended or adjusted under 35 U.S.C. 154(b) by 700 days.

(21) Appl. No.: 10/182,429

(22) PCT Filed: Dec. 4, 2000

(86) PCT No.: PCT/JP00/08580

§ 371 (c)(1),
(2), (4) Date: Oct. 14, 2002

(87) PCT Pub. No.: WO01/71663

PCT Pub. Date: Sep. 27, 2001

(65) Prior Publication Data

US 2003/0108230 A1    Jun. 12, 2003

(30) Foreign Application Priority Data

Mar. 23, 2000 (JP) .............................. 2000-081526
Apr. 27, 2000 (JP) .............................. 2000-128457

(51) Int. Cl.
G06K 9/00 (2006.01)
(52) U.S. Cl. .......................................... 382/128; 435/6
(58) Field of Classification Search ........ 382/128–134;
600/310, 407, 473, 476; 435/6, 7.1, 7.2,
435/7.21, 7.23, 40.5, 1.2, 40.51, 41, 70.1,
435/70.2, 70.3, 70.4, 440.449, 451–455;
436/63, 74, 94, 519; 424/9.2
See application file for complete search history.

(56) References Cited

U.S. PATENT DOCUMENTS 4,569,028 A    2/1986    Dolazza et al.

(Continued)

FOREIGN PATENT DOCUMENTS

DE    19801400 A1    7/1999

(Continued)

OTHER PUBLICATIONS

Schnabel, R., et al., "Assessing Normal Embryogenesis in *Caenorhabditis elegans* Using a 4D Microscope: Variability of Development and Regional Specification," *Developmental Biology* 184:234-265, 1997.

*Primary Examiner*—Jingge Wu
*Assistant Examiner*—Abolfazl Tabatabai
(74) *Attorney, Agent, or Firm*—Christensen O'Connor Johnson Kindness pllc

(57) ABSTRACT

The present invention provides a method for constructing cell lineage that is less labor intensive and requires less time as a result of using a computer. The method comprises the step for obtaining a plurality of 2D images different in focal plane and a time by taking a plurality of the 2D images by changing the focal plane and taking a plurality of the 2D images in a time series for a cell constituting the subject of observation. The method further comprises the steps of extracting a nucleus area by carrying out image processing for individual 2D images; unifying the nucleus area, which is derived from the identical nucleus, from the nucleus area extracted from the individual 2D images; and constructing the cell lineage from a time and a position, where the nucleus area appears and disappears in the image, in the unified nucleus area.

22 Claims, 17 Drawing Sheets

U.S. PATENT DOCUMENTS

| | | | | |
|---|---|---|---|---|
| 5,418,714 A | * | 5/1995 | Sarver | 600/407 |
| 5,643,761 A | * | 7/1997 | Fisher et al. | 435/91.1 |
| 5,667,981 A | * | 9/1997 | Groffen et al. | 435/7.23 |
| 5,766,948 A | * | 6/1998 | Gage et al. | 435/368 |
| 5,887,080 A | | 3/1999 | Tsubusaki et al. | |
| 5,917,936 A | | 6/1999 | Katto | |
| 6,051,376 A | * | 4/2000 | Fisher et al. | 435/6 |
| 6,110,666 A | * | 8/2000 | Grosveld et al. | 435/6 |
| 6,252,979 B1 | * | 6/2001 | Lee et al. | 382/133 |
| 2003/0013086 A1 | * | 1/2003 | Kask | 435/6 |

FOREIGN PATENT DOCUMENTS

| | | |
|---|---|---|
| JP | 60-164236 | 8/1985 |
| JP | 63212862 | 9/1988 |
| JP | 02016682 | 1/1990 |
| JP | 02-083785 | 3/1990 |
| JP | 06-096192 | 4/1994 |
| JP | 10-185911 | 7/1998 |
| JP | 2000028540 | 10/2000 |

* cited by examiner

Original Image  Resulting Image

CELL LINEAGE EXTRACTING METHOD

FIELD OF THE INVENTION

The present invention relates to a method for constructing cell lineage, and more specifically relates to a method for preparing cell lineage from a 4D-microscopic image of a subject of observation. Moreover, the present invention relates especially to a method of constructing cell lineage from 4D-microscopic images of an embryological stage of the nematode *Caenorhabditis elegans* (hereinafter referred to as *C. elegans*), with the images being taken using a Nomarski DIC microscope (hereafter referred to as a "Nomarski microscope").

BACKGROUND OF THE INVENTION

The nematode *C. elegans*, discovered by Sidney Brenner in 1965, is the experimental organism that has been analyzed in the most detail in modem molecular biology. *C. elegans* is the simplest organism among experimental multicellular organisms. It also requires only approximately 3 days until a fertilized egg becomes an adult.

With multicellular organisms, an adult made up from many cells is basically produced by repeated sequential cell division of a single fertilized egg (a single cell). A dendrogram of a division sequence starting from a fertilized egg is referred to as "cell lineage". *C. elegans* is the only multicellular organism for which cell lineage from a fertilized egg to adulthood has been clarified. This cell lineage was determined by Sulston et al. in 1983.

All normal (wild-type) *C. elegans* individuals exhibit identical cell lineage from egg fertilization to adulthood. In the case of mutation of specific genes, a change in the function of mutated genes causes a change in the pattern of cell division, i.e., cell lineage, from that of the wild type. A huge number of genes have been identified rapidly by an advance of research based on a presumption of the function of the mutated gene from the change of the cell lineage. The mass production of mutant animals has now begun. In consideration of the effective application of resources, automated analysis of cell lineage that is a starting point in the analysis of gene function is an essential technique.

For preparation of a conventional cell lineage, the so-called Nomarski microscope is used. In the Nomarski microscope, two beams of light (of identical wave form and phase, but having a very small difference in the light path) are generated by a set consisting of a polarizing plate and a Nomarski prism. The subject of observation is irradiated with these beams passing through the subject of observation. Differences in the refractive index of and optical path length through the sample produce different phases in the two beams of light after transmission. The two beams of transmitted light converge on the same optical path by the action of the set of polarizing plate and Nomarski prisms, but the phase difference between the two light beams causes interference. When using the Nomarski microscope, enhanced contrast produced by the action of interference facilitates observation. According to this method, the external shape and distribution of contents of a transparent subject is observed as contrasting light and dark areas. Biologically, cell content and external shape (cell membrane), both transparent when using a common optical microscope, can be observed as areas of light and dark.

Sulston et al determined the cell lineage of *C. elegans* by preparing a sketch from images observed under a Nomarski microscope with the unaided eye. This consumed a considerable amount of time (probably 1 year or more) and labor.

More recently, cell lineage is generally prepared using a 4D microscopic image produced by employing the Nomarski microscope. A microscopic image yielded from observations made at specific focal points is regarded as a 2D (x-y axis) sectional image obtained by the action of cutting the subject of observation horizontally in a specific position. That is, moving the focal point up and down (moving along the z axis) yields a sectional image produced by cutting the subject of observation in various slices along the z axis. Unifying these images allows the reconstruction of the 3D shape of the subject of observation (3D image). Moreover, collection of a time series of 3D images allows temporal changes in the subject of observation to be followed. An image taken in this manner is referred to as a "4D (4-dimensional) microscopic image".

Undoubtedly, present day methods for the construction of a 4D microscopic image are straightforward in comparison with those used at the time of Sulston's study. Nonetheless, considerable time and labor are still consumed, since decisions regarding the boundaries of the cell nucleus and cell membrane in the 4D image require input by the user. For example, a preparation from fertilized egg to 16-cells requires one day or more.

The present invention sets out to make conventional preparation of the cell lineage more straightforward and has an object of providing a method for constructing cell lineage that is less labor intensive and requires less time as a result of using a computer. A further object of the present invention is to improve the performance of a nucleus recognition process used when constructing the cell lineage by computer.

DISCLOSURE OF THE INVENTION

The present invention comprises the steps of: obtaining a plurality of 2D images different in a focal plane and a time by taking the plurality of the 2D images by changing the focal plane for a cell constituting the subject of observation and by taking a plurality of 2D images in a time series (i.e., obtaining a 4D microscopic image); extracting a nucleus area by carrying out image processing for individual 2D images; unifying the nucleus area, which is derived from the identical nucleus, from the nucleus area extracted from the above described individual 2D images (obtaining 4D unified nucleus area,) and constructing the cell lineage from a time and a position, where the nucleus area appears and disappears in the image, in the unified nucleus area (4D-unified nucleus area).

Preferably, the image is taken using a Nomarski DIC microscope. However, the image used is not restricted to that taken by this microscope.

Another technical means adopted by the present invention comprises the steps of: obtaining a plurality of 2D images different in a focal plane and a time by taking the plurality of the 2D images by changing the focal plane for a cell constituting the subject of observation and by taking a plurality of the 2D images in a time series (i.e., obtaining 4D microscopic image); extracting a nucleus area by carrying out image processing for individual 2D images; unifying the nucleus area, which is derived from the identical nucleus, from the nucleus area extracted from the above described individual 2D images (obtaining 4D unified nucleus area,) and constructing the cell lineage from the time and a position, where the nucleus area appears and disappears in the image, in the unified nucleus area (4D-unified nucleus area,) wherein the above described "step of extracting the nucleus area by carrying out image processing" has the steps of: extracting the area to become a candidate of the nucleus and designating a presumable nucleus area by a trial operation of cell lineage preparation and extracting the nucleus area by feedback of the presumable area to the nucleus candidate area.

Preferably, the trial operation of cell lineage preparation includes at least one of unifying nucleus areas in an identical time and an identical focal plane, unifying 4D nucleus areas, and preparing the cell lineage, thereby allowing feedback of the designation of the presumable nucleus area by the trial operation. For a process to unify identical nuclei in a plurality of images, viewing a near location temporally and spatially, the validity of a result of nucleus recognition can be tested. From the cell lineage produced, the location, in which the nucleus should exist or should not exist, can be presumed. The result of presumption is subjected to feedback to allow change of a parameter for recognition of the nucleus. In other words, a nucleus score for extracting the nucleus area from the nucleus candidate area is changed by feedback.

The step of extracting the nucleus comprises an approach for detecting an area, where the fine brightness variation in the image is poor, as the nucleus, or an approach for extracting a part, in which the change in the intensity is large in a wide range along the incident angle of the light, as the nucleus. The former is exemplified by that using a Kirsch filter, Prewitt filter, or FFT filter. The Kirsch filter is a filter prepared preferably by a combination of a Kirsch template type edge detection operator with moving average. The Prewitt filter is a filter preferably binarizing the output of a Prewitt template type edge detection operator and applying a distance transform. For the latter, the filter for taking a difference in a sum of intensity value of a predetermined top and bottom pixel along a seeming angle of light is adopted. The approach using the differential filter comprises the steps of extracting a cell boundary and extracting an embryo area and it is preferable to correct the result on the basis of the result of these steps.

The most preferable filter for extraction of the nucleus area is exemplified by an entropy filter. The entropy filter is the filter used to determine a starting point in an original image, partition the original image by a window having the size of a predetermined width and a predetermined height measured from the starting point, calculate an entropy of the window, and reserve this value as a form of coordinates of the image of the result. Partitioning the image by a small window and scanning the image calculating entropy of the window allows extraction of a flat part (a difference in a pixel value constituting the part is relatively small) as the nucleus area.

THE BEST MODE FOR CARRYING OUT THE INVENTION

[A] Cell Lineage Construction System

Figure 1:
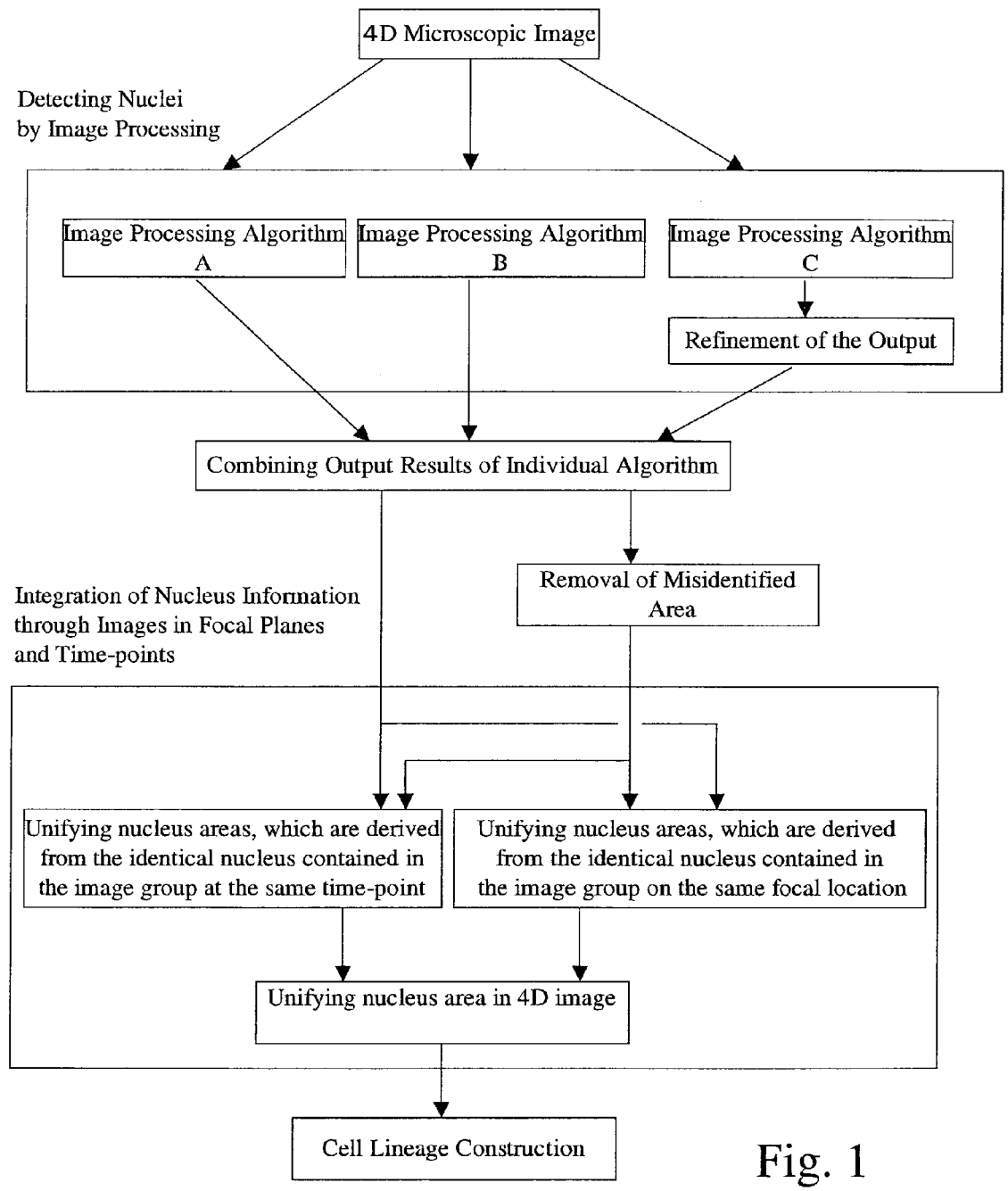
FIG. 1 is a flow chart of a method for extracting the cell lineage related to the present invention.

An embodiment of a method and a system for extracting cell lineage according to the present invention will be described below with reference to preparation of the cell lineage of a *C. elegans* early embryo. As shown in FIG. 1, the system has steps of [I] taking a Nomarski microscope 4D image of the *C. elegans* early embryo, [II] extracting a nucleus position in individual 2D images by employing image processing techniques applying a plurality of algorithms and combining the results of nucleus recognition according to each algorithm, [III] removing, if required, a misidentified nucleus area by operator intervention, [IV] unifying nucleus information of the image on a plurality of focal planes and in a plurality of times (time series) and [V] constructing the cell lineage on the basis of the time and position of emergence and disappearance of the 4D-unified nucleus area.

[I] Taking 4D Images

Figure 2:
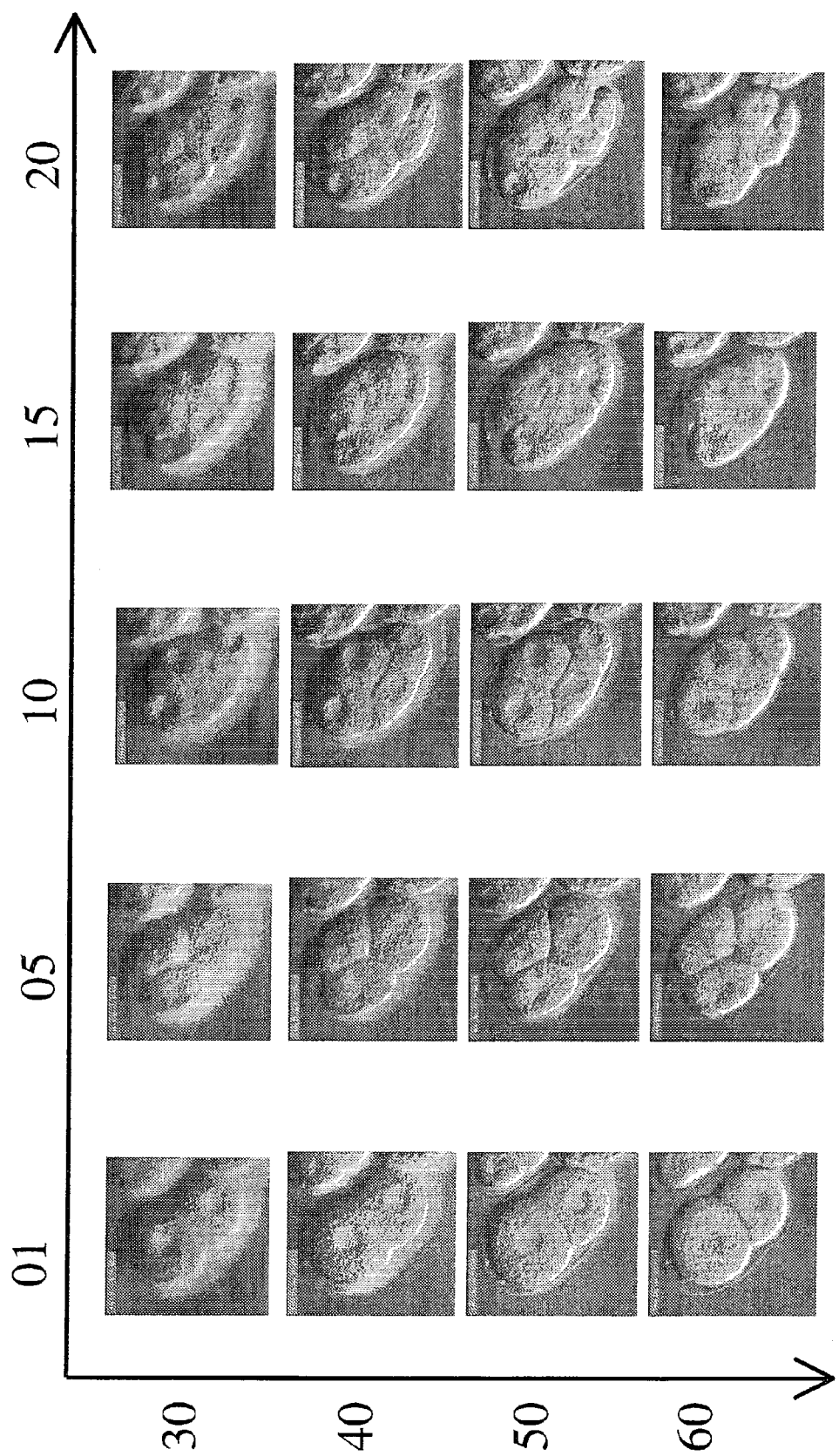
FIG. 2 is a view showing an example of a microscopic image of a subject of processing.

Taking a 4D image of the *C. elegans* early embryo using the Nomarski microscope will be described below. The 4D image is, as described in the foregoing Prior Art section, the plurality of the 2D images taken by changing the focal plane and the plurality of the 2D images taken in a time series. The image prepared by unifying the plurality of the 2D images having different focal planes and different times is called a 4D image. The *C. elegans* early embryo image, being a subject of processing in the present embodiment, is prepared as a set composed of 30 to 90 images obtained by changing the focal plane vertically in 1 to 5 minutes intervals. In an experiment, 1780 2D images in total were taken on 89 focal planes and at 20 points in the time series. The radial diameter was about 60 µm in the longer axis of a cell and about 30 µm in the shorter axis. Taking image was carried out every 90 seconds. FIG. 2 shows an example of the microscopic image of the subject of processing. Here, the horizontal axis is the time axis (time) and the vertical axis is the focal axis (focal plane).

[II] Extracting a Position of a Nucleus Using Nucleus Recognition Image Processing Algorithms Extracting a position of a nucleus in individual 2D microscopic images will be described below. Individual 2D microscopic images are processed using three kinds of image processing algorithms. The area recognized as a nucleus by any one of these three algorithms is determined as the nucleus area of the image processing system as a whole.

[Nucleus Recognition (Image Processing) Algorithm A]

This algorithm defines an area exhibiting poor fine variation in brightness in the microscopic image as the nucleus. In a Nomarski microscope image, the cytoplasm has the property of being an area rich in fine variation in brightness due to the presence of intracellular organelles, while the nucleus has the property of being an area poor in fine variation in brightness. The image processing algorithm A utilizes these properties. For capturing this characteristic, when an original image is converted by the Kirsch operator, an image is produced in which an area having low image contrast is expressed as an area having small brightness. The moving average method is then applied to the resultant image for data smoothing, and binarization processing is applied for separation of the area (nucleus) showing a small change of brightness from the cytoplasm.

The image processing algorithm A will be described in detail below. When the Kirsch edge detection operator is used to extract the area showing a large change of image brightness, a matrix showing the maximum output among the index matrices presented below is used.

$$\begin{pmatrix} 5 & 5 & 5 \\ -3 & 0 & -3 \\ -3 & -3 & -3 \end{pmatrix} \begin{pmatrix} 5 & 5 & -3 \\ 5 & 0 & -3 \\ -3 & -3 & -3 \end{pmatrix} \begin{pmatrix} 5 & -3 & -3 \\ 5 & 0 & -3 \\ 5 & -3 & -3 \end{pmatrix} \begin{pmatrix} -3 & -3 & -3 \\ 5 & 0 & -3 \\ 5 & 5 & -3 \end{pmatrix}$$

$$\begin{pmatrix} -3 & -3 & -3 \\ -3 & 0 & -3 \\ 5 & 5 & 5 \end{pmatrix} \begin{pmatrix} -3 & -3 & -3 \\ -3 & 0 & 5 \\ -3 & 5 & 5 \end{pmatrix} \begin{pmatrix} -3 & -3 & 5 \\ -3 & 0 & 5 \\ -3 & -3 & 5 \end{pmatrix} \begin{pmatrix} -3 & 5 & 5 \\ -3 & 0 & 5 \\ -3 & -3 & -3 \end{pmatrix}$$

For smoothing, the following formula is used.

$$g(x, y) + \frac{1}{m^2} \sum_{-(m-1)/2 \leq i, j \leq (m-1)/2} f(x+i, y+j)$$

Figure 3:
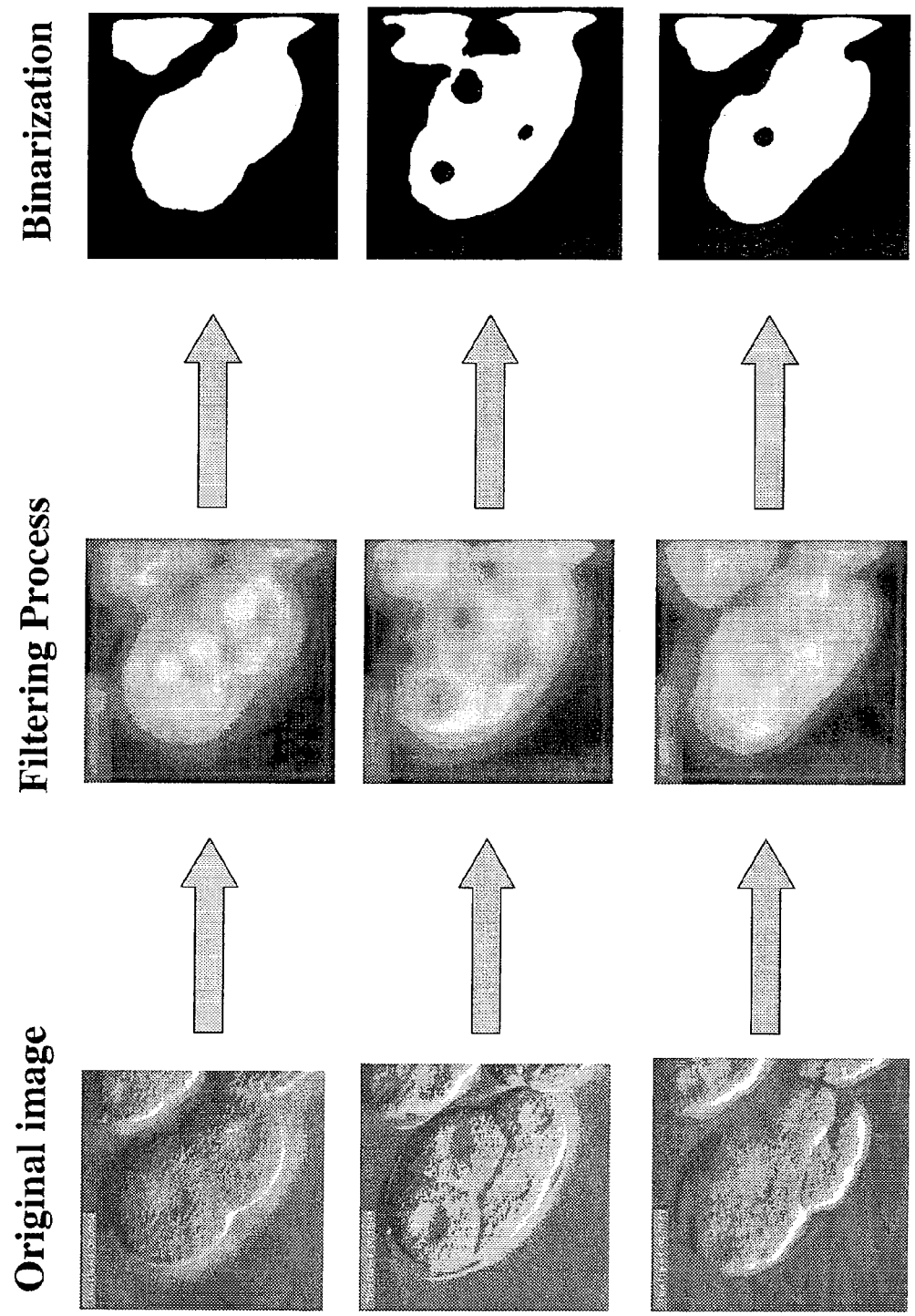
FIG. 3 is a view showing processing steps for a nucleus recognition algorithm A.

Following binarization, a connected-component having a shape like the nucleus is extracted. FIG. 3 shows the example.

[Nucleus Recognition (Image Processing) Algorithm B]

This algorithm also defines the area demonstrating poor fine variation in brightness in the microscopic image as the nucleus. When the original image is converted by the Prewitt template type operator and binarized, an image is produced depicting an area (cytoplasm) rich in brightness variation as an area where white dots are sparsely distributed and an area (nucleus) demonstrating poor brightness variation as a black area where no distribution of white dots is found. From this image, the area lacking the white dots is identified through distance transform processing.

Specifically, when the Prewitt template type edge detection operator is used to extract the area showing a large change of image brightness, a matrix showing the maximum output among the index matrices presented below is used.

$$\begin{pmatrix} 1 & 1 & 1 \\ 1 & -2 & 1 \\ -1 & -1 & -1 \end{pmatrix} \begin{pmatrix} 1 & 1 & 1 \\ 1 & -2 & -1 \\ 1 & -1 & -1 \end{pmatrix} \begin{pmatrix} 1 & 1 & -1 \\ 1 & -2 & -1 \\ 1 & 1 & -1 \end{pmatrix} \begin{pmatrix} 1 & -1 & -1 \\ 1 & -2 & -1 \\ 1 & 1 & 1 \end{pmatrix}$$

$$\begin{pmatrix} -1 & -1 & -1 \\ 1 & -2 & 1 \\ 1 & 1 & 1 \end{pmatrix} \begin{pmatrix} -1 & -1 & 1 \\ -1 & -2 & 1 \\ 1 & 1 & 1 \end{pmatrix} \begin{pmatrix} -1 & 1 & 1 \\ -1 & -2 & 1 \\ -1 & 1 & 1 \end{pmatrix} \begin{pmatrix} 1 & 1 & 1 \\ -1 & -2 & 1 \\ -1 & -1 & 1 \end{pmatrix}$$

Following binarization, the following median filter is used. FIG. 3 shows the example.

A median of:

$$g(x, y) = \{f(x + \Delta x, y + \Delta y)\}_{-m/2 \leq \Delta x \leq m/2, -m/2 \leq \Delta y \leq m/2}$$

Moreover, the following distance transform process is performed.

$$g(x, y) = \min \{d((x_1, y_1), (x, y)): f(x_1, y_1) \neq 0\}$$

Figure 4:
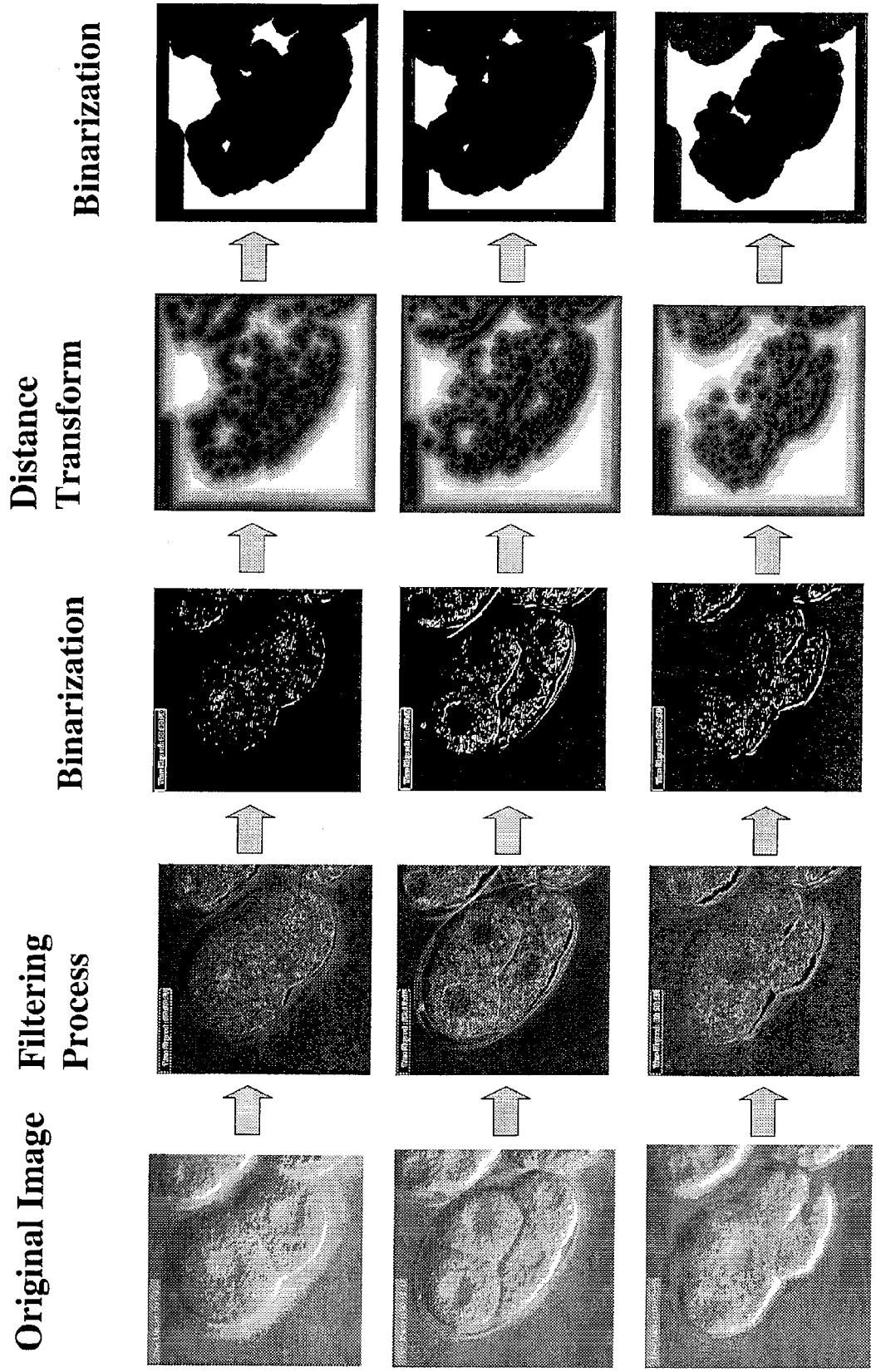
FIG. 4 is a view showing processing steps for a nucleus recognition algorithm B.

Then, binarization and connected-component processing are performed. An example of this is shown in FIG. 4.

[Nucleus Recognition (Image Processing) Algorithm C]

This algorithm uses the fact that the subject observed in the Nomarski microscope image is accompanied by a shadow that would be produced by lighting obliquely from the specified position. The nucleus membrane of a nucleus round in shape appears as a half light rim and half dark rim in the image. The region for which the change in the intensity is large in a wide range along the apparent direction of light is extracted as the nucleus. For example, the difference in total intensity value between the upward and downward 30 pixels along the apparent angle of incidence is assigned a value after transformation of the point. Binarizing the image after transformation makes the position of the nucleus visible as a white spot.

Specifically, a filter expressed by the following formula is applied to visualize the property that the nucleus appears surrounded by the light part and the dark part along the direction of light. Here, f(x, y) is intensity value of the original image, g(x, y) is intensity value of the converted image, θ is the direction of light, and m is a range of summation of intensity value.

$$g(x, y) = \frac{1}{2m} \sum_{k=-m}^{m} sgn(k) f(x + k\cos\theta, y - k\sin\theta)$$

Figure 5:
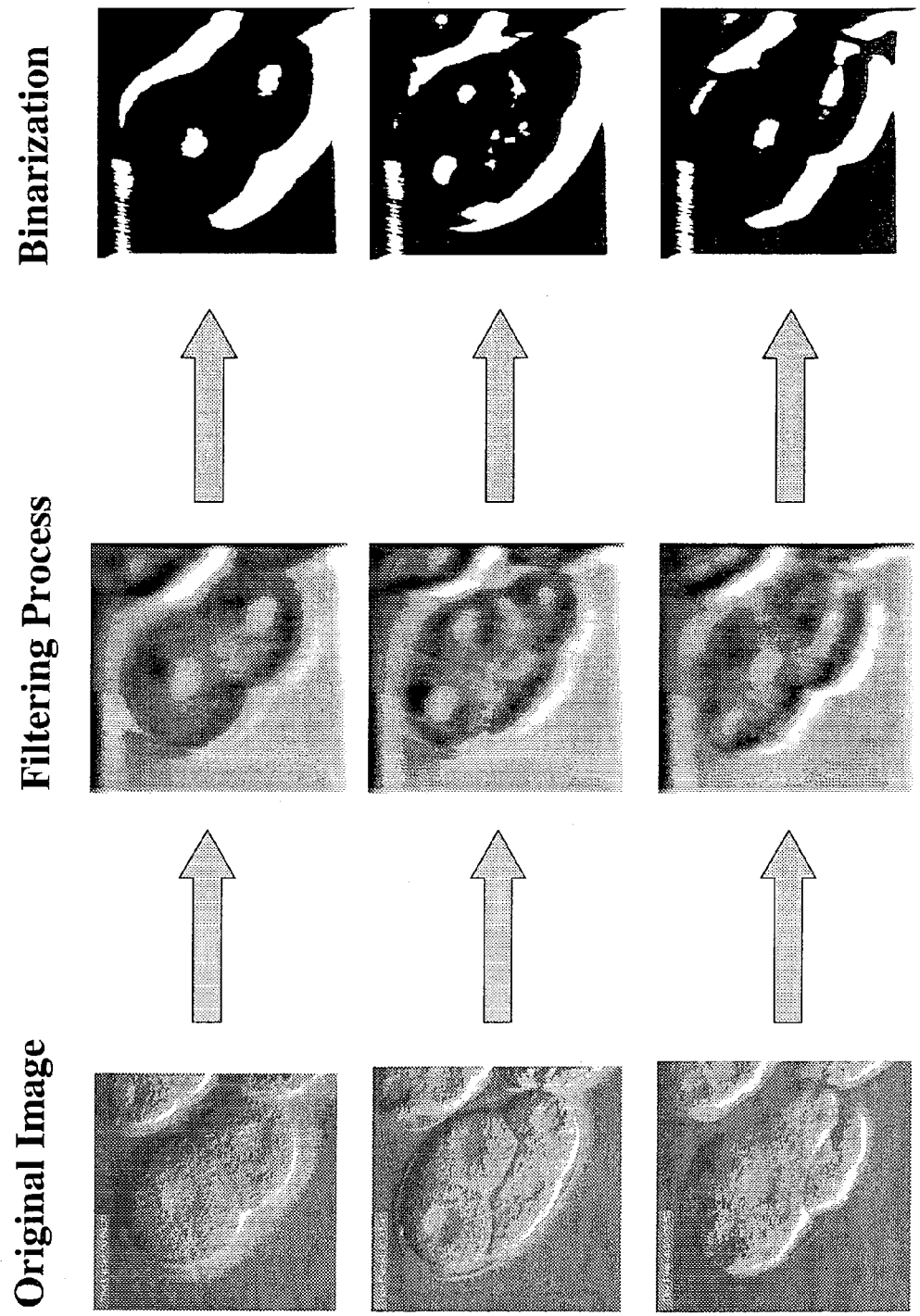
FIG. 5 is a view showing processing steps for a nucleus recognition algorithm C.

Following binarization, connected-component processing is performed. An example of this is shown in FIG. 5. As shown in FIG. 5, this filter can be easily used to produce a false positive on a boundary between cells and the outside of an embryo. Then, as mentioned below, a cell boundary and an embryo area are extracted for correction.

Figure 6:
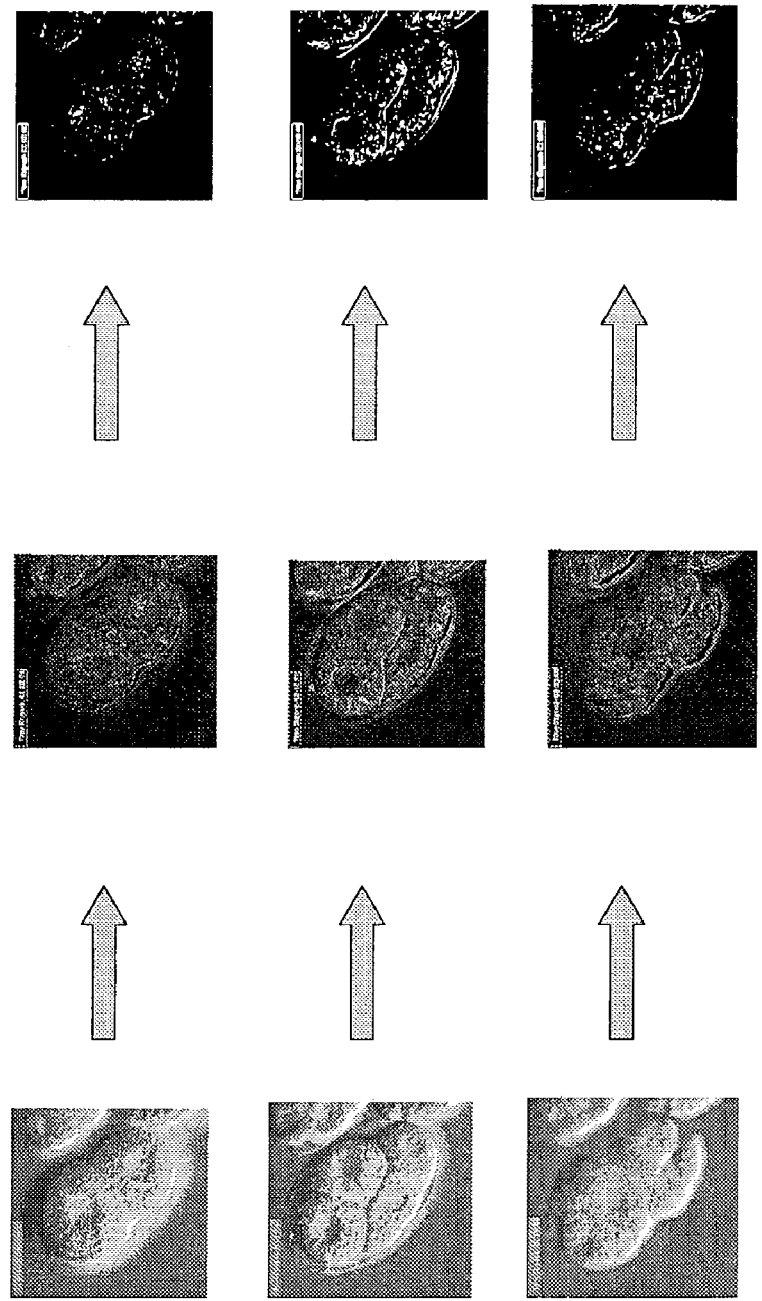
FIG. 6 is a view showing processing steps for a cell boundary detection algorithm.

The algorithm for detection of the cell boundary will be described below. The area evidently bordering cells is then searched so that the nucleus recognition algorithm C may be corrected. The result produced by the Prewitt template type edge detection operator is binarized. A degree of circularity, area, and a length of a circumference are employed to extract a slender area. The result is shown in FIG. 6.

Figure 7:
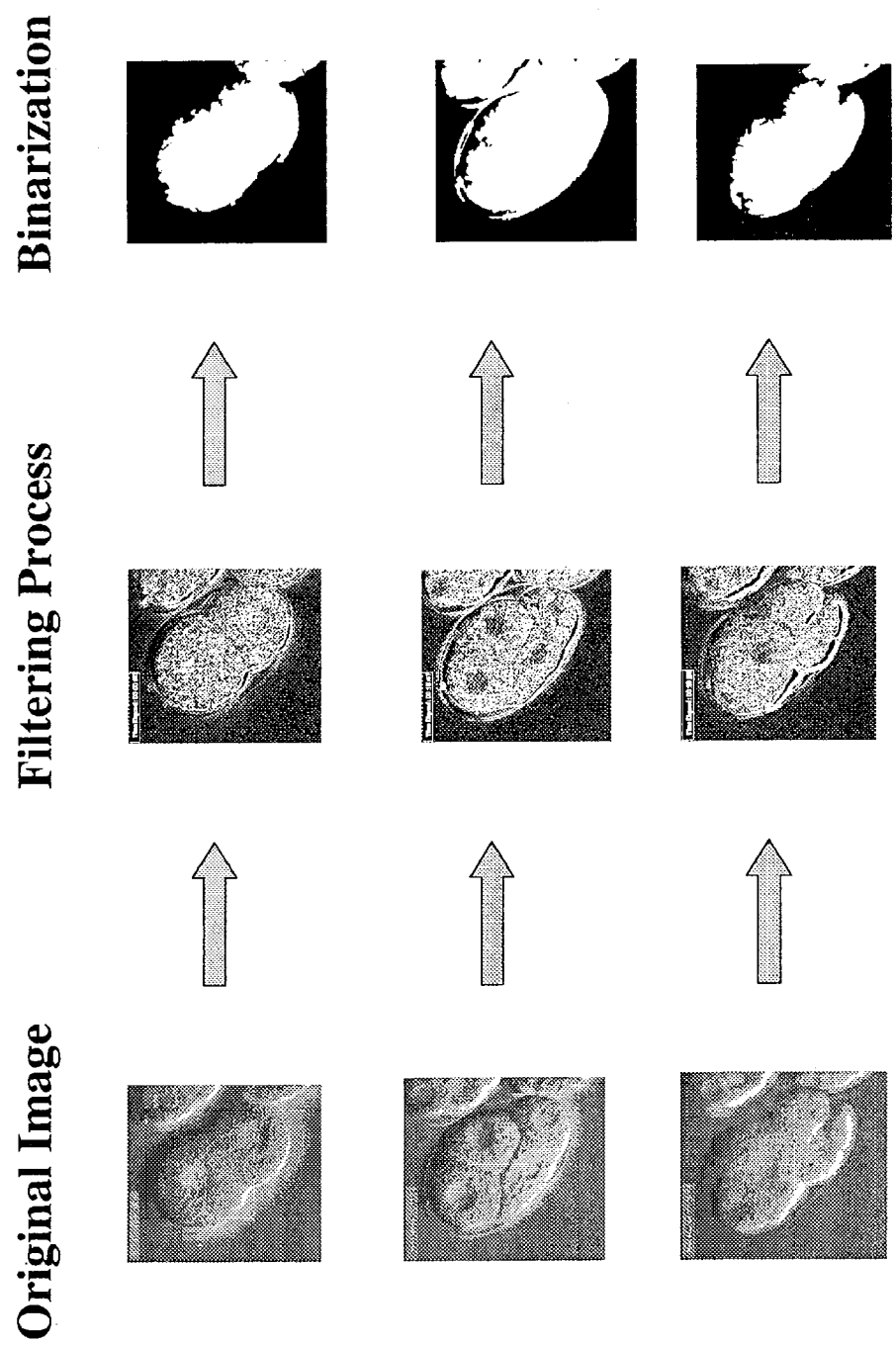
FIG. 7 is a view showing processing steps for an embryo area detection algorithm.

The algorithm for detection of an embryo area will now be described. The embryo area is then searched for in the image so that the nucleus recognition algorithm C can be corrected. The result produced by the Kirsch template type edge detection operator is binarized. The maximum connected-component is extracted. The result is shown in FIG. 7.

Nucleus information recognized by the three kinds of algorithm described above is combined. As described above, the area recognized as the nucleus by any one of the three kinds of algorithm is judged as the nucleus area by the whole image processing system.

[III] Removing a Misidentified Nucleus Area

Next, from the result of automated nucleus recognition, any misidentified nucleus area is manually removed. The above described image processing algorithm is incomplete, since in accordance with an increase in the number of cells, some areas (false positives) are recognized erroneously as the nucleus area. It is difficult to build up the cell lineage correctly from data containing many false positives. The present system includes a tool for manually removing the false positives (which is an area misidentified by the nucleus recognition algorithm, in other words, an area recognized as a place where a nucleus exists by the algorithm despite there not being a real nucleus) from the result of the above described image processing. This GUI tool will be described based on FIG. 8 to FIG. 10.

Figure 8:
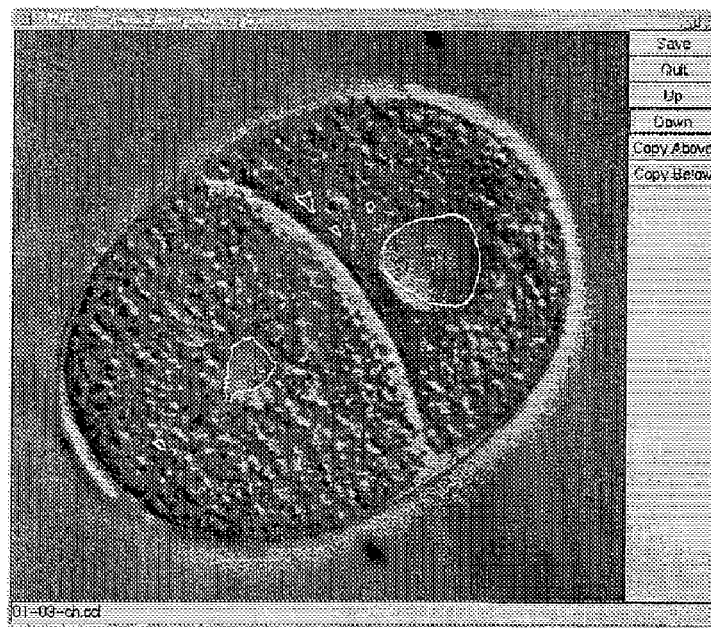
FIG. 8 is a view showing a tool for manual correction of a result of automated nucleus recognition.
Figure 9:
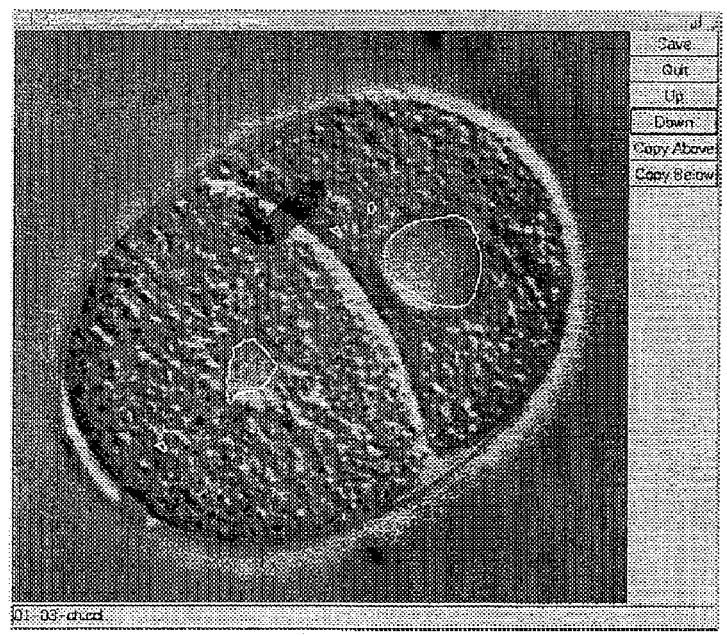
FIG. 9 is a view showing the tool for manual correction of the result of automated nucleus recognition.
Figure 10:
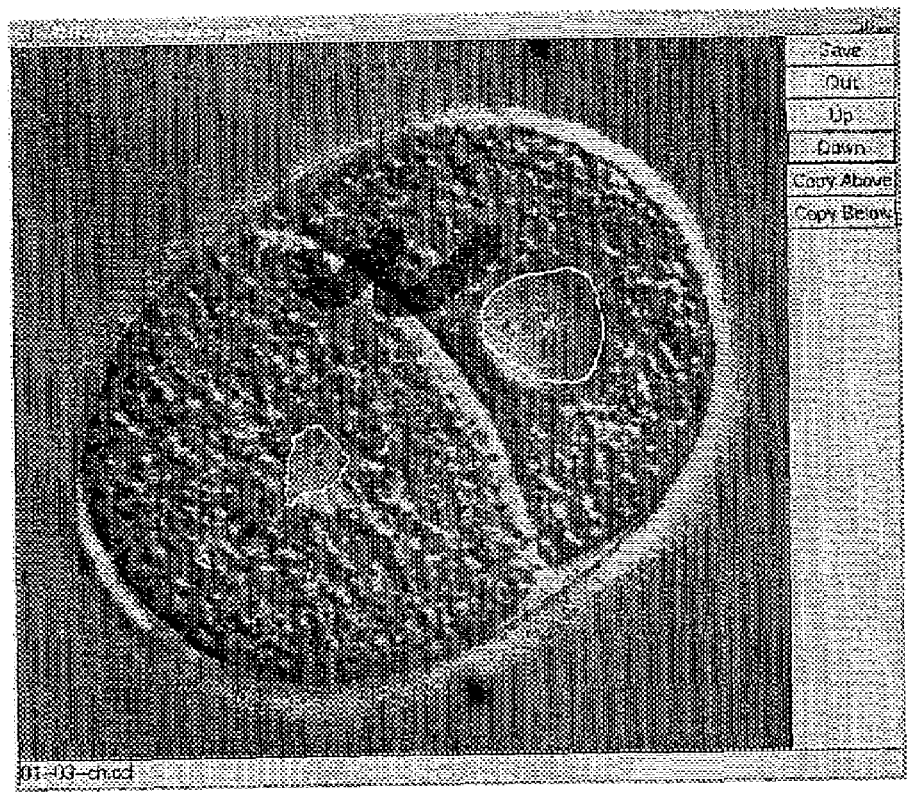
FIG. 10 is a view showing a tool for manual correction of the result of automated nucleus recognition.

First, as shown in FIG. 8, the results for each nucleus recognition algorithm are unified and the area (the area surrounded by a white line) recognized as a "nucleus area" is displayed through superimposition on the original image (display of the result of nucleus recognition.) Next, as shown in FIG. 9 and FIG. 10, a "nucleus area" which has been misidentified is filled in using a mouse (the misidentified nucleus area is traced pressing a button on the mouse) to eliminate the misidentified nucleus area ("removal of the misidentified nucleus area.") Finally, the nucleus area information incorporating the result of the removal of the misidentified nucleus area is stored in a file format usable for the subsequent preparation of cell lineage. The false positive removal operation can be carried out in a straightforward manner by applying this tool. By this practice, false positives were removed from 1780 images in about one hour. It is obvious that manual processing is not an essential constitutional element of the technological concept of the present invention. However, this step can be omitted by improving the accuracy of automated nucleus recognition.

[IV] Unifying Nucleus Areas

Figure 11:
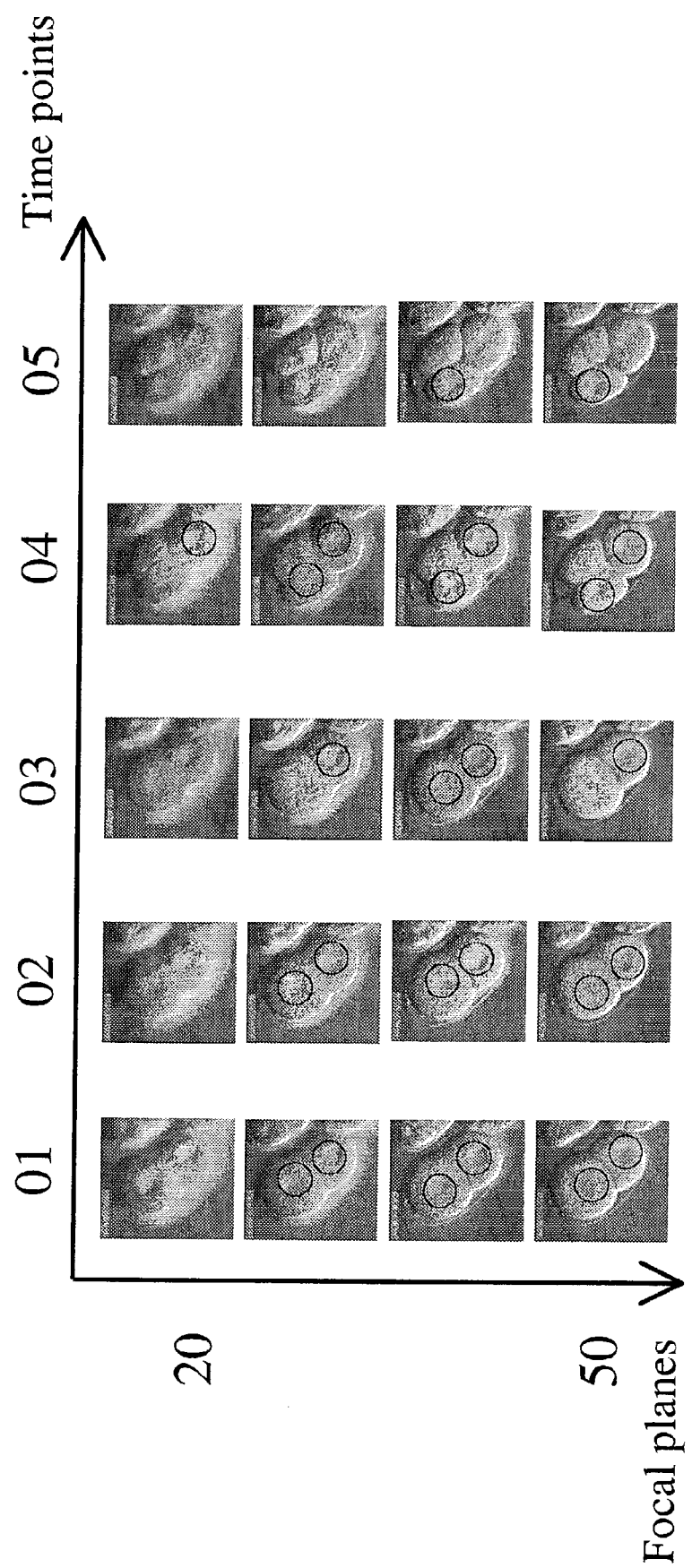
FIG. 11 is a view illustrating a step of unifying identical nuclei within a plurality of images.

The process of unifying nucleus areas, which are derived from identical nuclei, recognized in different 2D images will be described below. From the result of recognition in the 2D images, in order to know when and where which nucleus emerges and disappears in the image, identical nuclei recognized in different 2D images are unified. This example is shown in FIG. 11. Here, the horizontal axis is the time axis (time) and the vertical axis is the focal axis (focal plane).

[Unifying Nucleus Areas, Which are Derived from Identical Nuclei, Contained in an Image Group on an Identical Focal Plane]

For the time series image group (having the same coordinate value on the z axis) taken from the identical focal plane, specific nucleus areas which are derived from identical nuclei (i.e., nucleus areas which correspond to temporal changes of identical nuclei) are unified. When nucleus areas N, N' are detected on coordinates (x, y), (x', y'), the 2D distance dxy of N, N' is defined as follows, and a condition of deciding derivation of nucleus areas from the identical nucleus is set.

$$d_{xy}(N,N') = \sqrt{|x-x'|^2 + |y-y'|^2}$$

By using this condition, unifying is sequentially carried out starting at the earliest time where individual nuclei are detected. That is, at an identical focal point, the result of nucleus recognition in the time series is unified into one set. The steps are as follows.

1. Select the nucleus that emerges at the earliest time.
2. At the next time, nuclei, between which the 2D distance is the shortest and found to be less than or equal to the previously assigned threshold (25 pixels in our current system), are identified as those (successor) derived from the identical nucleus and unified.
3. Repeat the operation of 2 until no nucleus derived from the identical nucleus is found.
4. Repeat the operations from 1 to 3 until no more nuclei remain.

[Unifying Nucleus Areas, Which are Derived from Identical Nuclei, Contained in an Image Group at an Identical Time]

Similar to the above described method, nucleus area, derived from the identical nucleus and contained in the image group having different focal planes (coordinate z) at identical times are unified. The results of recognition of nuclei on different focal planes at the identical time are unified into one set. The threshold of distance is 10 pixels.

[Unifying Nucleus Areas, Which are Derived from Identical Nuclei, that Appear in all 4D Images]

Figure 12:
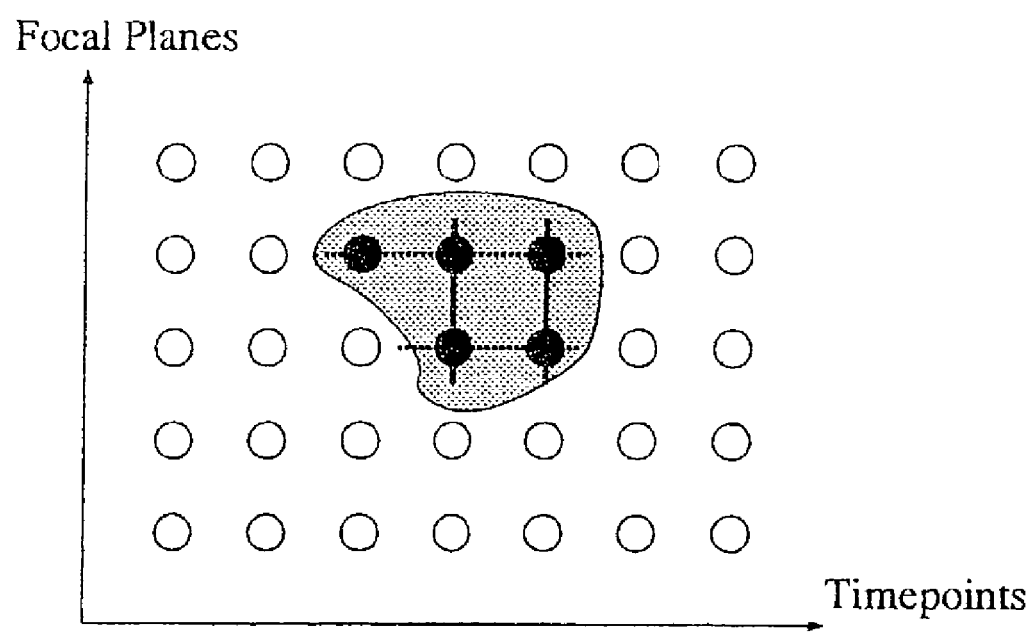
FIG. 12 is a view illustrating a step of unifying identical nuclei within a plurality of images, similar to FIG. 11.

In the case where there exists a combination of unified nucleus areas, which have a common nucleus area, between the nucleus areas (unified nucleus area) unified in both the time series and the focal direction, these are regarded as a unified nucleus area derived from an identical nucleus, and are further unified (a nucleus area unified in a 4D image is referred to as a 4D-unified nucleus area.) When unifying sets which contain the same nucleus, among individual sets, which have been unified in an image group having the same focal points and in an image group having the same times, into one set, such a set, in which five or fewer images are recognized, is regarded as a fragment, and is not used for constructing the cell lineage. FIG. 12 is a view illustrating unification of nucleus area. An open circle shows an image in which a predetermined nucleus was not observed and a solid circle shows an image in which the predetermined nucleus was observed. A longitudinal solid line indicates one set recognized as the identical nucleus. A transverse dotted line indicates one set recognized as the identical nucleus.

[V] Constructing the Cell Lineage

Figure 13:
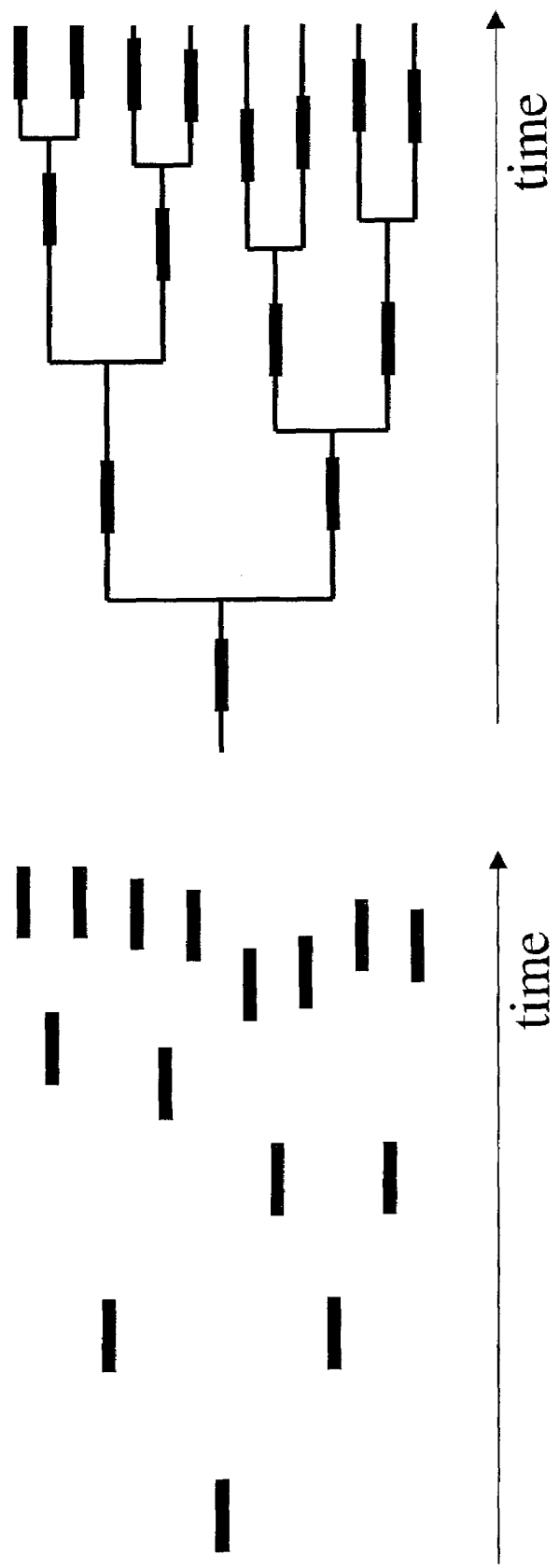
FIG. 13 is a view illustrating a step in the construction of the cell lineage from nucleus information.

The 4D-unified nucleus area contains information about the time and position of emergence and disappearance of the nucleus in the image. The cell lineage is constructed based on this information (FIG. 13.) A nucleus emerging for the first time is assigned to a root. When two cells (daughter cells) produced after cell division of a certain cell (parent cell) are sought, the time and position of disappearance of a parent cell nucleus in the image is obtained from the corresponding 4D-unified nucleus area, and the 4D distance from the time and position of emergence of all the 4D-unified nucleus areas other than that above described is calculated. In order to add to the cell lineage, the two closest 4D-unified nucleus areas are assigned to daughter cells. However, in the case where the 4D distance is larger than a specified value, they are not regarded as daughter cells.

Specifically, the following steps are applied.
1. Choose the nucleus (may be plural) showing the earliest time of emergence to add to the cell lineage. This becomes the root of the cell lineage.
2. Choose a nucleus showing the earliest time of disappearance from the nucleus already included in the cell lineage. This is assigned to Np.
3. Choose two nuclei, between which 4D distance is shortest and between which the distance is less than or equal to the threshold (100) from Np, to add to the cell lineage as daughter cells.
4. Repeat steps 2 to 3 until extending the cell lineage becomes impossible.

Where, if two nucleus areas appear in t1, t2 at positions (x1, y1, z1) and (x2, y2, z2), 4D distance d in each of these two areas is defined by the following equation. cz and ct are weightings of distances in temporal and spatial directions and specific values of cz and ct are 2 and 10, respectively.

$$d((x1,y1,z1,t1), (x2,y2,z2,t2)) = \sqrt{(x_1-x_2)^2 + (y_1-y_2)^2 + c_z^2(z_1-z_2)^2 + c_t^2(t_1-t_2)_2}$$

[B] Cell Lineage Construction System Having a Feedback Mechanism

Figure 14:
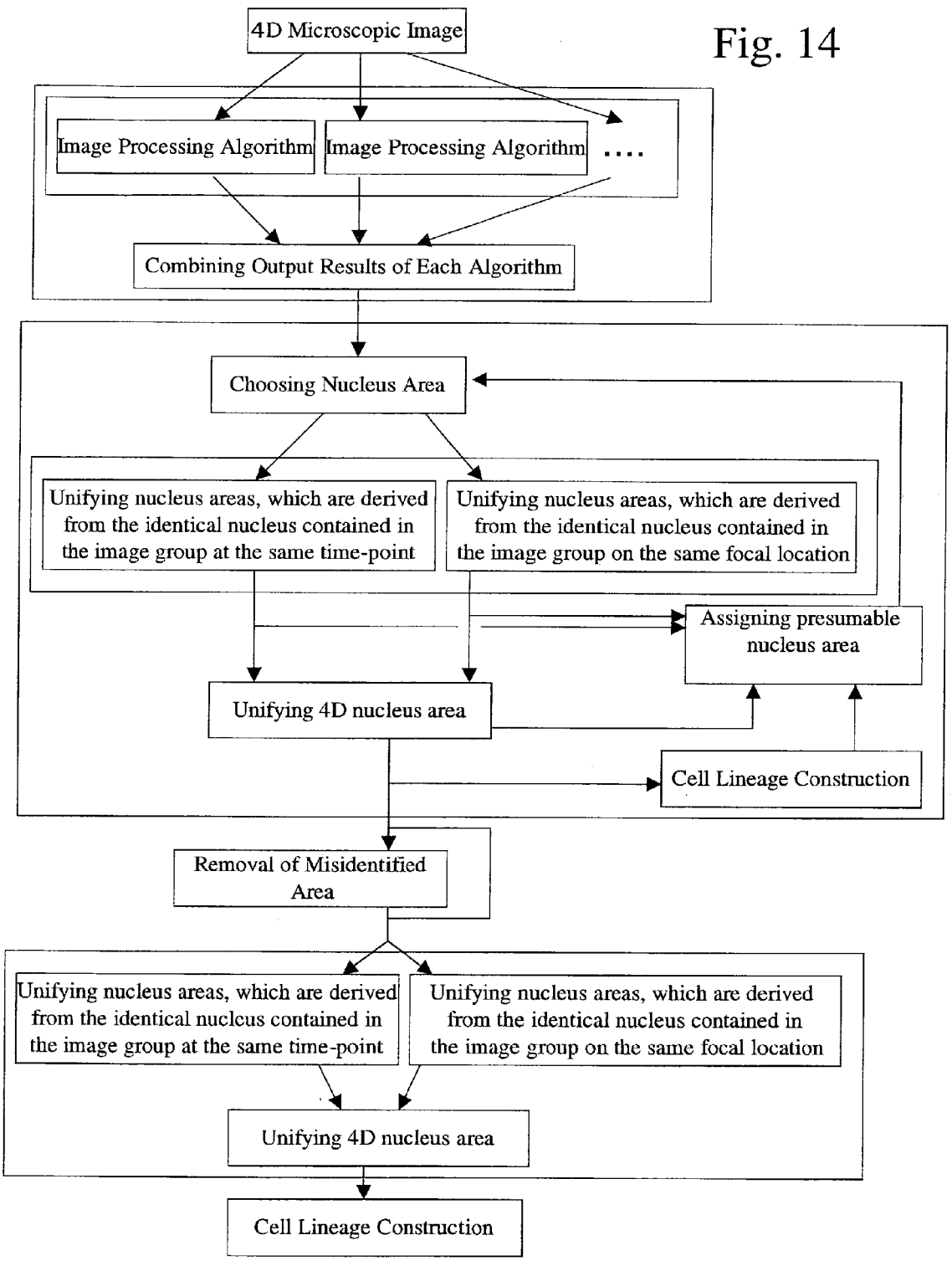
FIG. 14 is a flow chart of a method for extracting the cell lineage related to another embodiment of the present invention.

Another embodiment of a method and system for extracting the cell lineage in accordance with the present invention will be described below with reference to cell lineage preparation of the early embryo of *C. elegans*. FIG. 14 is a block diagram of the system, wherein the system comprises [I] a step for taking a Nomarski microscope 4D image of the *C. elegans* early embryo, [II] designating a nucleus candidate area according to the image processing algorithm for nucleus recognition, [III] a mechanism for choosing the nucleus area using the feedback mechanism, [IV] if required, a step of manually removing the misidentified area, and [V] a step of unifying the nucleus information taken from the image in a plurality of focal planes and a plurality of times (time series), i.e. a unifying algorithm of the nucleus area derived from the identical nucleus, and [VI] a step of constructing the cell lineage from the temporal and spatial information of emergence and disappearance of the 4D unified nucleus area.

[I] Taking 4D Images

For imaging of the 4D image of the *C. elegans* early embryo using the Nomarski microscope, the description of the first embodiment can be cited as is.

[II] Assigning the Nucleus Candidate Area Through the Nucleus Recognition Image Processing Algorithm The nucleus recognition image processing algorithm is classified into two categories: an image processing algorithm group; and an algorithm unifying the result of image processing. For the image processing algorithm group, the description of the first embodiment can be cited as is. In conclusion, the nucleus recognition algorithm A, the nucleus recognition algorithm B, and the nucleus recognition algorithm C can be adopted.

Next, the algorithm unifying the result of image processing will be described below. Using a 4D microscopic image, the area (the nucleus candidate area) where presence of the nucleus is determined, is extracted and a likelihood score (a nucleus score.) is given. As a specific current method, (a) threshold method and (b) polar area method are adopted.

[Threshold Method]

This method is for binarizing the result of an individual image processing algorithm using each specific threshold and designating the nucleus candidate area. The area assigned is scored (nucleus score) according to its area and roundness. For the result of the algorithm C, the area prepared by correction is scored according to its area and roundness.

[Polar Area Method]

For the result (before binarization) of individual image processing algorithms, gray levels (normally used for 256 levels of gray) are assigned to every pixel of the image to make a nucleus portion appear darkish (also in a filter to make each portion appear whitish, this state is produced by reversing black and white). Polar areas in a direction of black in this image are extracted accompanying a score. Polar areas in a direction of black is the area, where (i) each pixel value in the area shows a higher black degree than that of each value of the pixels adjacent to a contour of the area and (ii) the area falls in a predetermined round shape (using the value almost equal to a size of the nucleus in the image is most preferable). Its score depends on darkness and the total area of each pixel in the area. This operation is independently conducted for each algorithm to unify the result of image processing using suitable weighting. These pole areas in a direction of black and their scores are defined as the nucleus candidate area and the nucleus score of the candidate area, respectively. The image before binarization was smoothed and subjected to distance transformation in the case of a Kirsch filter and a Prewitt filter, respectively. In case of algorithm C, there are three types of methods applicable to pole area method. (i) Performing detection and scoring, as performed with the other algorithms, of the nucleus area by using the "approach of taking the difference in intensity value," (ii) recognizing the area, considering only that which is identified as an embryo area in areas detected in (i), as the nucleus area by applying the "embryo area detection algorithm," and (iii) recognizing the area, considering only that which is identified as the embryo area in areas detected in (i) and not the cell boundary as recognized by applying the "cell boundary detection algorithm," as the nucleus area by applying the "embryo area detection algorithm."

[III] A Mechanism for Choosing the Nucleus Area Using the Feedback Mechanism

The nucleus recognition feedback will be described below. This algorithm uses the nucleus candidate area having a nucleus score, which is prepared by the above described algorithm to unify the result of image processing, as input and employs feedback of the result of the cell lineage preparation work thereafter to extract the nucleus area (the area determined as the place where the nucleus resides). Specifically, using feedback of each trial work of (i) unifying nucleus areas present at an identical time and on an identical focal plane, (ii) unifying 4D nucleus areas, and (iii) constructing the cell lineage, in this order to extract finally the nucleus area. Feedback can be partially omitted.

Feedback data is used as information for changing the nucleus score while comparing a "nucleus score (the score of likelihood of being the nucleus)" with "a specified value." The term "specified value" is for a specific value given before executing the program. The specified value influences the performance of the feedback system and an optimal value should therefore be selected. In the current system, an image algorithm is applied to several examples of a 4D microscopic image sample, and the value obtained in the absence of misidentification (i.e., the value indicating real nuclei for all nucleus areas detected) is used.

Flow of the feedback mechanism will be described below. First, "feedback (i) from an operation of unifying nucleus areas present at an identical time and on the identical focal plane" is performed. By this, the nucleus score of the nucleus candidate areas included in the area decided as a presumable nucleus area is increased by the value assigned for this feedback. As the result, among these nucleus candidate areas, those of which nucleus score exceeds the specified value of the nucleus score in "a case of operating after algorithms for unifying the result of image processing" are decided as nucleus areas. On the other hand, for those not exceeding this specified value, the nucleus score for the increase is discarded and reassigned to the nucleus score of the original value for recovery as one of the nucleus candidate areas. Next, the nucleus areas containing the nucleus area newly added in such a manner is input to a subsequent process to repeat feedback from "the operation of unifying nucleus areas present at an identical time and on the identical focal plane." When no new nucleus areas are added by this feedback mechanism after repeating the feedback, then "an operation of unifying the 4D nucleus areas (ii)" is executed. In this feedback, the nucleus score unique to this feedback is added to the nucleus candidate area. In a similar manner to that described above, this feedback is carried out until no new nucleus area is added. Following this stage, feedback from "the operation of constructing the cell lineage (iii)" is carried out until the new nucleus area is no longer added by this feedback mechanism. In order that the feedback functions effectively, the value of the nucleus score added to the nucleus candidate area in each feedback should be as (i)<(ii)<(iii). Each kind of feedback will now be described individually in the following.

[Feedback from the Operation of Unifying Nucleus Areas Present at an Identical Time and in an Identical Focal Plane]

This process includes three processes: (a) choosing nucleus areas, (b) unifying nucleus areas at an identical time and on the identical focal plane, and (c) designating the presumable nucleus area.

(a) Choosing Nucleus Areas (i) In the Case of Operation After the Algorithms for Unifying the Result of Image Processing The nucleus candidate area, of which nucleus score exceeds the specified value, is determined to be the nucleus area. All nucleus candidate areas and nucleus areas are stored together with the nucleus score thereof.

(ii) In the Case of Working After Feedback

Among nucleus candidate areas previously stored, the nucleus score of those of which a centroid is contained in the presumable nucleus area supplied by feedback is increased for the specified value. Thereafter, the nucleus candidate area, of which nucleus score exceeds the specified value, is determined to be the new nucleus area through adding to the nucleus area previously stored. The nucleus area information is updated together with the nucleus score.

(b) Unifying Nucleus Areas at an Identical Time and in an Identical Focal Plane

Unification of nucleus areas derived from the identical nucleus area recognized for different 2D images will be described below. From the result of recognition for 2D images, in order to know when and where which nucleus emerges and disappears in the image, the identical nuclei recognized in different 2D images are unified (refer to FIG. 11.).

(i) Unifying Nucleus Areas Derived from the Identical Nucleus Contained in the Image Group on the Identical Focal Plane For the group of images (which are equal to each other in the value of the z axis coordinate) taken on the identical focal plane in a time series, those derived from the identical nucleus (nucleus areas for which temporal change of the identical nucleus is pursued) in each nucleus area of these images are unified. When nucleus areas N and N' are detected from the coordinates (x, y), (x', y'), 2D distance dxy of N, N' is defined as follows and the condition of deciding derivation of nucleus areas from the identical nucleus is set.

$$d_{xy}(N,N')=\sqrt{|x-x'|^2+|y-y'|^2}$$

Using this distance, the unifying procedure is sequentially operated starting from the earliest time where individual nuclei are detected. Namely, at the identical focal point, the result of nucleus recognition in the time series is unified into one set. The steps are as follows.

1. Select the nucleus that emerges at the earliest time.
2. At the next time, nuclei, between which the 2D distance is the shortest and found to be less than or equal to the previously assigned threshold (25 pixels in our current system), are identified as those (successor) derived from the identical nucleus and unified.
3. Repeat the operation of 2 until no nucleus derived from the identical nucleus is found.
4. Repeat the operations from 1 to 3 until all nuclei have been unified.

(ii) Unifying Nucleus Areas Derived from the Identical Nucleus Contained in the Image Group at the Identical Time Similar to the above described method, the nucleus areas derived from the identical nucleus and contained in the image group having different focal planes (coordinate z) at an identical time are unified. The results of recognition of nuclei in different focal planes at the identical time are unified into one set. The threshold of distance in the current system is 10 pixels in this case.

(c) Designating the Presumable Nucleus Area

When the nucleus area is present in a certain focal plane, the nucleus area derived from the nucleus, which is identical to that in the nucleus area, is highly probably present on the adjacent top and bottom focal planes at the identical time. Specifically, in consideration of a certain nucleus area, a coordinate (Xc, Yc) of a centroid of the nucleus area is taken and the area of the radial diameter R around the coordinate (Xc, Yc) in the adjacent top and bottom images at the identical time is decided as the presumable nucleus area. In our current system, R is set to the radial diameter of a standard nucleus. The image is similarly worked on at the adjacent time on the identical focal plane. In other words, for the above described nucleus area, a circular area with a radial diameter R around the coordinate (Xc, Yc) in the adjacent images on the identical focal plane and at the identical time is decided as the presumable nucleus area.

(d) Feedback

The presumable nucleus area yielded from the result of (c) is fed to (a) to repeat operations from (a) to (d). Following several feedback operations, a 3D nucleus area yielded from (b) is transferred to the next step of unifying 4D nucleus areas.

[Feedback from Operation of Unifying 4D Nucleus Areas]

This process includes four processes: (a) choosing 3D nucleus areas, (b) 4D-unifying nucleus areas, (c) designating the presumable nucleus area, and (d) feedback.

(a) Choosing 3D Nucleus Areas

Feedback from the operation of unifying nucleus areas present in the above described identical time and in the identical focal plane is continued until any effect disappears.

(b) 4D Unification of Nucleus Areas

In the case where there exists a combination of unified nucleus areas, which have a common nucleus area, between the nucleus areas (unified nucleus area) unified in both the time series and the focal direction, these are regarded as a unified nucleus area derived from an identical nucleus, and are further unified (a nucleus area unified in a 4D image is referred to as a 4D-unified nucleus area.) When unifying the sets, which contain the identical nucleus, among individual sets, which have been unified in the image group having the identical focal plane and the image group having the identical time, into one set, the set, in which five or fewer images are recognized, is regarded as a fragment and not used in the cell lineage. FIG. 12 is a view illustrating unification of nucleus area. An open circle shows an image in which the predetermined nucleus was not observed and the solid circle shows an image in which the predetermined nucleus was observed. The longitudinal solid line indicates one set recognized as the identical nucleus. The transverse dotted line indicates one set recognized as the identical nucleus.

(c) Assigning the Presumable Nucleus Area

The presumable nucleus area is assigned using information concerning an adjacent focal plane and information concerning an adjacent time. Specifically in our current system, in the case where there exists an area, in which the nucleus area derived from the identical nucleus is present in 3 or more images among 4 images (2 images in the identical time and the adjacent focal plane and 2 images in the identical focal plane and the adjacent time), an area of union of a circular area with the radial diameter R around the centroid of these nucleus areas is assigned to the presumable nucleus area.

(d) Feedback

The presumable nucleus area yielded from the result of (c) is fed to (a) to repeat operations from (a) to (d). Following several feedback operations, a 4D-unified nucleus area yielded according to (b) is transferred to the next cell lineage-preparing operation step.

[Feedback from the Operation of Preparing the Cell Lineage]

This process includes 4 processes: (a) choosing 4D nucleus areas, (b) preparing the cell lineage, (c) designating the presumable nucleus area, and (d) feedback.

(a) Choosing 4D Nucleus Areas

The operation of feedback from the operation of unifying the above described 4D nucleus areas is continued until any effect disappears.

(b) Preparing Cell Lineage

In this process, the two processes of (i) construction of a triple-parent-daughter relationship among 4D-nucleus areas and (ii) construction of pair-parent-daughter relationship among 4D-nucleus areas are onerated in this order (i) Construction of a Triple-Parent-Daughter Relationship Among 4D-nucleus areas In this process, three 4D-nucleus areas showing a parent nucleus and its two daughter nuclei after cell division are identified.

4D-nucleus areas are represented by $N_1, N_2, \ldots N_n$. Each 4D nucleus area (Ni) contains the following information.

Time of emergence $T_{ei}$: the earliest time in which the image appears in the 4D nucleus area.

Time of disappearance $T_{di}$: the latest time in which the image disappears in the 4D nucleus area.

Position of emergence $P_{ei}=(X_{ei}, Y_{ei}, Z_{ei})$: (X, Y, Z) coordinates of the centroid of 3D nucleus area in the time of emergence.

Position of disappearance $P_{di}=(X_{di}, Y_{di}, Z_{di})$: (X, Y, Z) coordinates of the centroid of 3D nucleus area in the time of disappearance.

From all existing 4D nucleus areas, a set of three 4D nucleus areas is made in all possible combinations. Among individual sets of 4D nucleus areas, those showing the earliest disappearance time are assigned to parent 4D nucleus areas ($N_m$) while the remainder are assigned to daughter 4D nucleus areas ($N_{d1}, N_{d2}$). The score (a triple-parent-daughter score), expressing the possibility that these three combinations of 4D nucleus areas are real sets of parent-daughter nuclei, is calculated.

In our current system, the score reflects (i) the time of disappearance of the parent 4D-nucleus area and the time of emergence of the two daughter 4D-nucleus areas, (ii) the distance between the position of disappearance of the parent 4D-nucleus area and positions of emergence of the two daughter 4D-nucleus areas, and (iii) positional relationship between the position of disappearance of the parent 4D-nucleus area and the positions of emergence of two daughter 4D-nucleus areas (particularly, whether the disappearance position of the parent 4D-nucleus area is close or not to a midpoint of the emergence position of two 4D-daughter cells.) Specifically, the current score $F_3(N_m, N_{d1}, N_{d2})$ is given as follows.

$$F_3(N_m, N_{d1}, N_{d2}) = -K_{3t}((T(N_m, N_{d1}) - C_{3t})^2 + (T(N_m, N_{d2}) - C_{3t})^2)$$
$$-K_{3s}((S(N_m, N_{d1}) - C_{3s})^2 + (S(N_m, N_{d2}) - C_{3s})^2)$$
$$-K_{3v}\frac{V(N_m, N_{d1}) \cdot V(N_m, N_{d2})}{|V(N_m, N_{d1})||V(N_m, N_{d2})|}$$

where $T(N_1, N_2)$=(Disappearance time of N1)–(emergence time of N2)

$S(N_1, N_2)$=Distance between (Disappearance position of N1) and (emergence position of N2)

$\sqrt{(X_{d1}-X_{e2})^2+(Y_{d1}-Y_{e2})^2+(Z_{d1}-Z_{e2})^2}$ $V(N_1, N_2)$=Vector from (disappearance position of N1) to (emergence position of N2)

$(X_{e2}-X_{d1}, Y_{e2}-Y_{e1}, Z_{e2}-Z_{e1})$ $K_{3t}, K_{3s}, K_{3v}, C_{3t}, C_{3s}$ are appropriate constants.

As described above, the triple-parent-daughter score of all existing three 4D-nucleus areas is calculated, the triple-parent-daughter relationship is decided in descending order of merit with regards the scoring result, and until a combination occurs with a score below the threshold is produced, these operations are sequentially repeated. When a conflicting parent-daughter relationship occurs, priority is given to the parent-daughter relationship with a good scoring result.

(ii) Construction of a pair-parent-child relationship among the 4D-nucleus area.

Two sets of 4D-nucleus areas, which express either the parent nucleus or one of two daughter nuclei after cell division, are searched from 4D-nucleus areas in which at least any one of a parent or her daughter has not been determined in (i).

All possible sets of two are prepared from 4D-nucleus areas in which at least any one of the parent or daughter has not been determined in (i). Among those sets of 4D-nucleus areas, those showing an earlier disappearance time are assigned to parent 4D-nucleus areas (Nm) and the remaining to daughter 4D-nucleus areas (Nd, Nd.) The score (a pair-parent-daughter score) of the possibility that a combination of these two 4D-nucleus areas is the real set of parent and daughter nuclei is calculated.

In our current system, the score reflects i) the time of disappearance of the parent 4D-nucleus area and the time of emergence of the two daughter 4D-nucleus areas and ii) the distance between the position of disappearance of the parent 4D-nucleus area and positions of emergence of the two daughter 4D-nucleus areas. Specifically, the current score $F_2(N_m, N_d)$ is given as follows.

$$F_2(N_m, N_d) = K_{2t}((T(N_m, N_d) - C_{2t})^2) - K_{2s}((S(N_m, N_d) - C_{2s})^2)$$

where, $K_{2t}$, $K_{2s}$, $C_{2t}$, $C_{2s}$ are appropriate constants.

As described above, the pair-parent-daughter score of two 4D-nucleus areas are all calculated, and the combination showing an achievement better than the score being the threshold are determined as demonstrating a pair-parent-daughter relationship.

(c) Assigning the Presumable Nucleus Area

The presumable nucleus area is assigned by using the triple-parent-daughter relationship and the pair-parent-daughter relationship.

(i) Assigning the Presumable Nucleus Area by Using the Three-Nucleus-Area Parent-Daughter Relationship In the 4D-nucleus area set of which the three-nucleus-area parent-daughter relationship has been decided, using the disappearance time of the parent 4D-nucleus area and the time of emergence of two daughter 4D-nucleus areas, the presumable nucleus area is assigned. It is considered that in the nucleus area contained in individual 4D-nucleus areas, the disappearance time of the parent 4D-nucleus area and the time of emergence of two daughter 4D-nucleus areas, the possibility of the presence of the nucleus area derived from the nucleus identical to its nucleus area on the adjacent top and bottom focal planes at the identical time and at the time immediately before and after is high. Specifically, in consideration of the nucleus area at the time of emergence or the time of disappearance, the coordinates (Xc, Yc) of the centroid of the nucleus area are taken and the area with the radial diameter R is decided as the presumable nucleus area and a simultaneous point thereof, the image on the adjacent top and bottom focal planes, and the identical focal plane, the image immediately before and after the adjacent time, the area with the radial diameter R around each coordinate (Xc, Yc) is assigned to the presumable nucleus area. R is set to the radial diameter of the standard nucleus in our current system.

(ii) Designating the Presumable Nucleus Area by Using the Pair-Parent-Daughter Relationship It is assumed that for sets of the 4D nucleus area for which the pair-parent-daughter relationship has been decided, the presumable nucleus area is designated using the time of disappearance of the parent 4D nucleus area and the time of emergence of the daughter 4D nucleus area. In the nucleus area included in individual 4D nucleus areas at the time of disappearance of the parent 4D nucleus area and the time of emergence of the daughter 4D nucleus area, a higher probability of the presence of the nucleus area derived from the identical nucleus is observed on the adjacent top and bottom focal planes at the identical time and at the time immediately before and after on the identical focal planes. A specific method is the same as that of (i).

At the time of emergence of the daughter 4D nucleus area, it is assumed that the higher probability of emergence of another daughter cell is observed around the position that is symmetric with respect to the emerged position of the daughter 4D nucleus area, with the position of disappearance of the parent 4D nucleus area as a center, and accordingly, the presumptive nucleus area is assigned. Specifically, at the time of emergence of the daughter cell and at the times immediately before and after, a circular area with the radial diameter R around the position that is symmetric with respect to the above described position of the daughter cell is assumed as a presumptive nucleus area. In the current system, R is set to the radial diameter of the standard cell.

(d) Feedback

The presumptive nucleus area yielded from the result of (c) is fed to (a) to repeat operations from (a) to (d). After several cycles of this feedback operation, the unified 4D nucleus area yielded in (b) is outputted to the next step as the output of a nucleus area choosing mechanism by a feedback mechanism.

[IV] Removal of Misidentified Nucleus Areas

Subsequently, the misidentified nucleus areas are manually removed from the results of automatic nucleus recognition. Please refer to the description of the first embodiment and FIG. 8 to FIG. 10 for details. This step is not essential for the present invention.

[V] Unifying Nucleus Information

Unifying nucleus information derived from identical nuclei recognized in different 2D images will be described below. Identical nuclei recognized in different 2D images are unified in order to know from the result of recognition of the 2D images, when and where each nucleus emerges and disappears in the image. For unifying nucleus information, the description of the first embodiment is referable and FIG. 11 can be taken into consideration. In FIG. 11, the horizontal axis is the time axis (time) and the vertical axis is the focal axis (focal plane).

[Unifying Nucleus Areas Derived from an Identical Nucleus Contained in the Image Group in the Identical Focal Plane]

With a group of images taken in the identical focal plane in a time series (equal to each other in the value of the z axis coordinate), nucleus areas (for which temporal change of the identical nucleus is pursued) derived from the identical nucleus in each nucleus area of these images are unified. When nucleus areas N and N' are detected from the coordinates (x, y). (x', y'), 2D distance dxy of N, N' are defined as follows and the condition of deciding derivation of nucleus areas from the identical nucleus is set.

$$d_{xy}(N, N') = \sqrt{|x-x'|^2 + |y-y'|^2}$$

Using this 2D distance, the unifying process is sequentially executed starting from the earliest time where individual nuclei are detected. Namely, at the identical focal point, the result of nucleus recognition in the time series is unified into one set. The steps are as follows.

1. Select the nucleus that emerges the soonest.
2. At the next time, unified nuclei, between which the shortest 2D distance, i.e. distance dxy, is stored, and for which this distance is below a previously assigned appropriate threshold (25 pixels in our current system), nuclei are identified as those (successor) derived from the identical nucleus.
3. Repeat the operation of 2 until no nucleus derived from the identical nucleus is found.
4. Repeat the operations from 1 to 3 until all nuclei have been unified.

[Unifying Nucleus Areas Derived from the Identical Nucleus Contained in the Image Group on the Identical Time]

Similar to the above described method, the nucleus area, derived from the identical nucleus and contained in the image group having different focal planes (coordinate z) at the identical time, is unified. The results of the recognition of nuclei on different focal planes at the identical time are unified into one set. The threshold of distance in our current system is 10 pixels in this case.

[Unifying Nucleus Areas Derived from the Identical Nucleus Appearing in all 4D Images]

In the case where a combination of the unified nucleus area having the nucleus area commonly possessed by the nucleus areas unified (unified nucleus area) at each time series and focal direction exists, those are regarded as the unified nucleus area derived from the identical nucleus and a decision is made to unify them further (the nucleus area unified in the 4D image is called 4D-unified nucleus area.) Among individual sets unified in the image group on the identical focal point and at the identical time, any set recognized only in five or fewer images while unifying sets containing the identical nucleus into one set is regarded as a fragment and is not used for the cell lineage. FIG. 12 is the view illustrating unification of nucleus areas. The open circle shows the image in which a predetermined nucleus was not observed and the solid circle shows the image in which the predetermined nucleus was observed. The longitudinal solid line indicates one set recognized as the identical nucleus. The transverse dotted line indicates one set recognized as the identical nucleus.

[VI] Constructing the Cell Lineage

The 4D-unified nucleus area contains information about the time and position of emergence and disappearance of the nucleus in the image. The cell lineage is constructed on the basis thereof (FIG. 13). For construction of the cell lineage, the approach of the first embodiment may be used. However, a different approach is adopted in the second embodiment. In this process, two sub-processes of (i) construction of the triple-parent-daughter relationship of the 4D nucleus area and (ii) construction of the pair-parent-daughter relationship of 4D nucleus area, are operated in this order.

(i) Construction of the Triple-Parent-Daughter Relationship of the 4D Nucleus Area.

In this process, three 4D-nucleus areas showing the parent nucleus and two daughter nuclei after cell division are searched.

4D-nucleus areas are represented by $N_1, N_2, \ldots N_n$. Each 4D nucleus area (Ni) contains the following information.

Time-point of emergence $T_{ei}$: the earliest time at which the image emerges in the 4D nucleus area.

Time-point of disappearance $T_{di}$: the latest time at which the image disappears in the 4D nucleus area.

Position of emergence $P_{ei}=(X_{ei}, Y_{ei}, Z_{ei})$: (X, Y, Z) coordinates of the centroid of 3D nucleus area at the time of emergence.

Position of disappearance $P_{di}=(X_{di}, Y_{di}, Z_{di})$: (X, Y, Z) coordinates of the centroid of 3D nucleus area at the time of disappearance.

From all existing 4D nucleus areas, the set of three 4D nucleus areas is made in all possible combinations. Among individual sets of 4D nucleus areas, those showing the earliest disappearance time are assigned to the parent 4D nucleus areas ($N_m$) and the remainder are assigned to daughter 4D nucleus areas ($N_{d1}, N_{d2}$.) The score (a triple-parent-daughter score) expressing the possibility, in that these three combinations of 4D nucleus areas are real sets of parent-daughter nuclei, is calculated.

In our current system, the score reflects (i) the time of disappearance of the parent 4D-nucleus area and the time of emergence of two daughter 4D-nucleus areas, (ii) the distance between the position of disappearance of the parent 4D-nucleus area and positions of emergence of two daughter 4D-nucleus areas, and (iii) relation between the position of disappearance of the parent 4D-nucleus area and the positions of emergence of two daughter 4D-nucleus areas (particularly, whether or not the disappearance position of the parent 4D-nucleus area is close to the midpoint of the emergence position of the two 4D-daughter cells.) Specifically, the current score $F_3(N_m, N_{d1}, N_{d2})$ is given as follows.

$$F_3(N_m, N_{d1}, N_{d2}) = -K_{3t}((T(N_m, N_{d1}) - C_{3t})^2 + (T(N_m, N_{d2}) - C_{3t})^2)$$
$$-K_{3s}((S(N_m, N_{d1}) - C_{3s})^2 + (S(N_m, N_{d2}) - C_{3s})^2)$$
$$-K_{3v}\frac{V(N_m, N_{d1}) \cdot V(N_m, N_{d2})}{|V(N_m, N_{d1})||V(N_m, N_{d2})|}$$

where
$T(N_1, N_2)$=(Disappearance time of N1)–(emergence time of N2)
$S(N_1, N_2)$=Distance between (Disappearance position of N1) and (emergence position of N2)

$$\sqrt{(X_{d1}-X_{e2})^2+(Y_{d1}-Y_{e2})^2+(Z_{d1}-Z_{e2})^2}$$

$V(N_1, N_2)$=Vector from (disappearance position of N1) to (emergence position of N2)

$$(X_{e2}-X_{d1}, Y_{e2}-Y_{e1}, Z_{e2}-Z_{e1})$$

$K_{3t}, K_{3s}, K_{3v}, C_{3t}, C_{3s}$ are appropriate constants.

As described above, the triple-parent-daughter score of all existing three 4D-nucleus area is calculated, and the triple-parent-daughter relationship is decided in descending order of merit with respect to the scoring result, and these operations are sequentially repeated until a combination is produced with a score below the designated threshold. When a conflicting parent-daughter relationship occurs, a higher priority is given to the parent-daughter relationship with the highest scoring result.

(ii) Construction of the Pair-Parent-Daughter Relationships Among the 4D-Nucleus Area Two sets of 4D-nucleus areas, specifically those expressing the parent nucleus and one of two daughter nuclei after cell division, are searched from 4D-nucleus areas in which at least any one of the parent or the daughter has not been determined in (i).

All possible twin sets are prepared from 4D-nucleus areas in which at least any one of the parent or the daughter has not been determined in (i). Among those sets of 4D-nucleus areas, those showing the earlier disappearance time are assigned to the parent 4D-nucleus areas (Nm) and the rest are assigned to daughter 4D-nucleus areas (Nd, Nd). The score (a pair-parent-daughter score) of the possibility that the combination of these two 4D-nucleus areas is the set of real parent and daughter nuclei is calculated.

In the current system, the score reflects (i) the time of disappearance of the parent 4D-nucleus area and the time of emergence of two daughter 4D-nucleus areas and (ii) a distance between the position of disappearance of the parent 4D-nucleus area and positions of emergence of two daughter 4D-nucleus areas. Specifically, the current score $F2(N_m, N_d)$ is given as follows.

$$F_2(N_m, N_d) = -K_{2t}((T(N_m, N_d) - C_{2t})^2) - K_{2s}((S(N_m, N_d) - C_{2s})^2)$$

where, $K_{2t}$, $K_{2s}$, $C_{2t}$, $C_{2s}$ are appropriate constants.

As described above, the pair-parent-daughter score of two 4D-nucleus areas are all calculated and those that achieve scores higher than the threshold are determined to demonstrate a two-nucleus-area parent-daughter relationship.

[C] Other Nucleus Area Extraction Filters

In the above described two embodiments, three image processing algorithms have been applied as the nucleus recognition filter. However, the nucleus recognition filter used in the present invention is not restricted to these. Other embodiments of the nucleus recognition filter will be described below.

[Entropy Filter]

Figure 15:
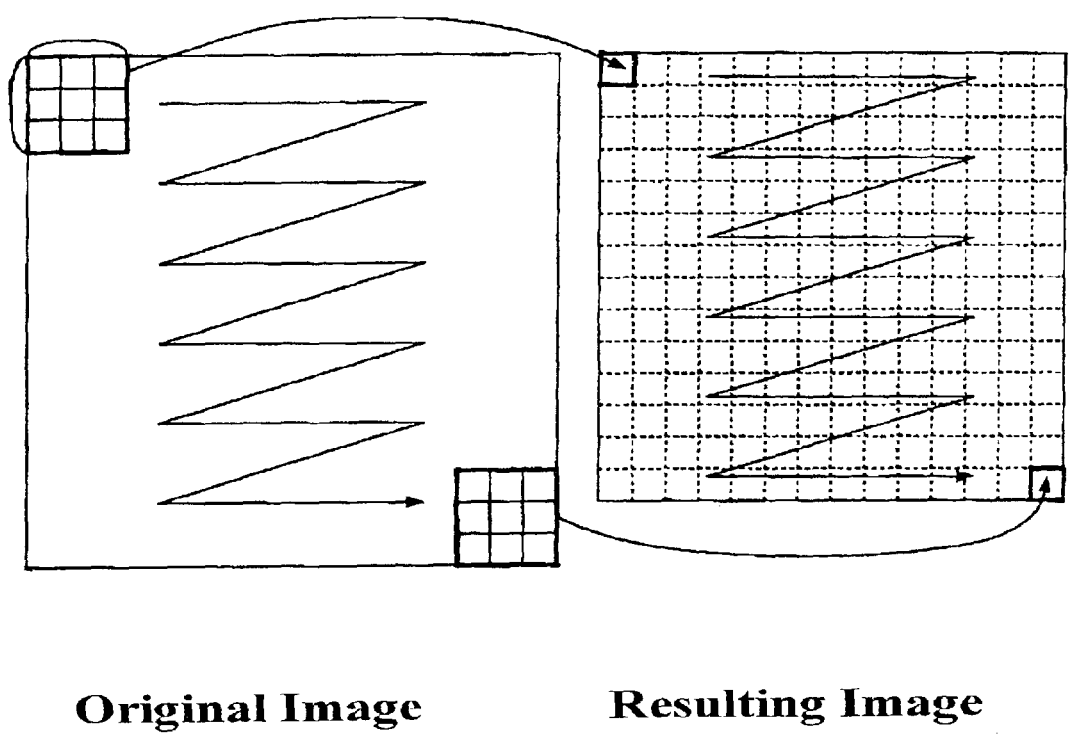
FIG. 15 is a view illustrating an entropy filter.
Figure 16:
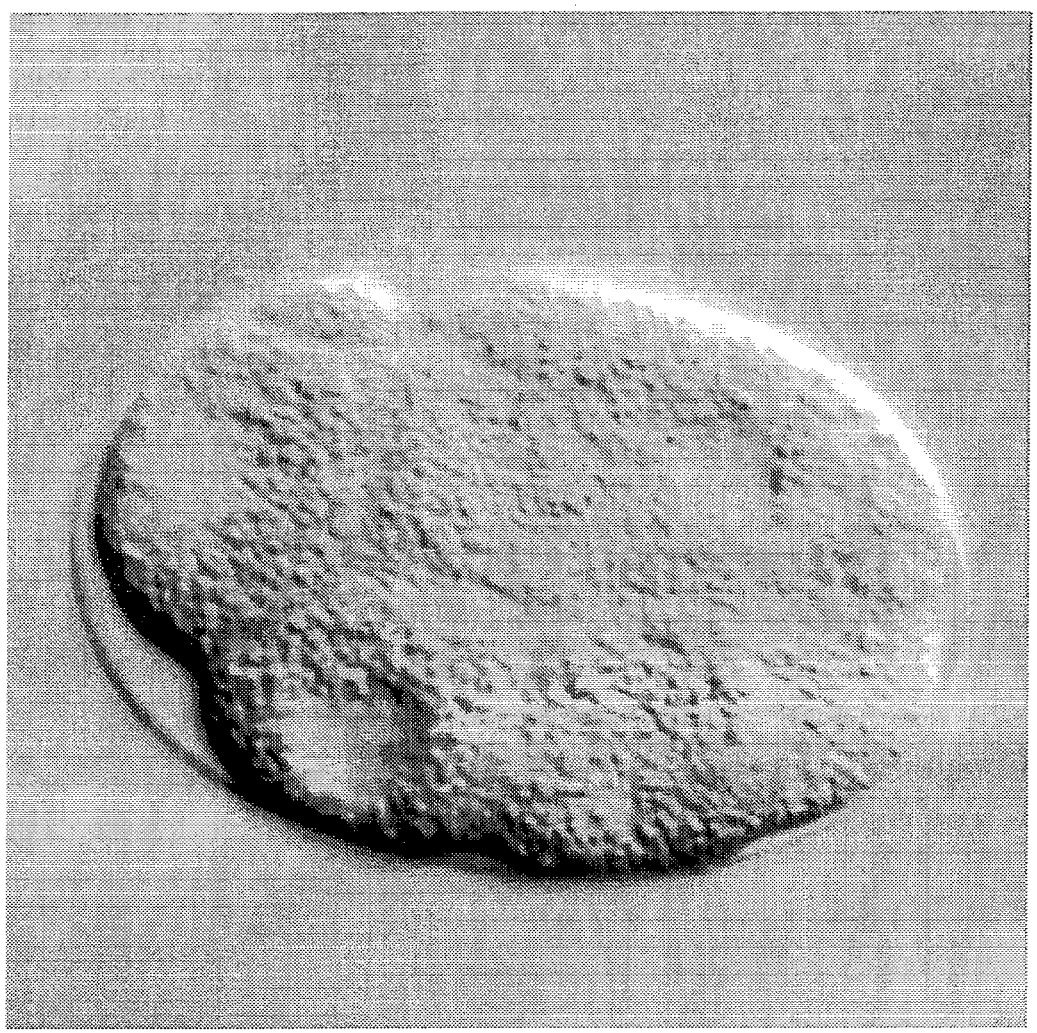
FIG. 16 is a microscopic image of a cell.

FIG. 16 is the microscopic image of a *C. elegans* early embryo taken using the Nomarski DIC microscope. The cytoplasmic portion (which is coarse in quality) shows a relatively large difference in gray level, while the nucleus portion (which is relatively smooth in quality) shows a relatively small difference in gray level. The entropy filter is that for efficient extraction of the smooth portion from the image. This employs the property that the cytoplasmic portion is coarse in image quality, while, in contrast, the nucleus portion is relatively smooth in image quality. As shown in FIG. 15, a start point (x, y) is determined in the original image. X is ranged from 0 to (image width minus window width) and y is ranged from 0 to (image height minus window height.) Next, the image is partitioned by a window of size (width, height)=(A, B) from the start point. Entropy of the window partitioned is calculated to save on the coordinates (x, y) of a resulting image.

Entropy is calculated based on the following equation.

$$EPY = -\sum_{l=l\min}^{l\max} P(l) \log P(l)$$

In the formula, P(1) is a gray level histogram produced using a gray level histogram H (1) for the image area as a measure of its characteristics (if a gray level is L, 1=0, 1, 2, ..., L−1), and dividing the frequency of each gray level by the total number of frequency (a pixel number N of the image area), and then normalizing to make the total pixel number into 1.0. After calculation of and comparison with a reference entropy value, the nucleus area is discriminated from the cytoplasmic area.

Figure 17:
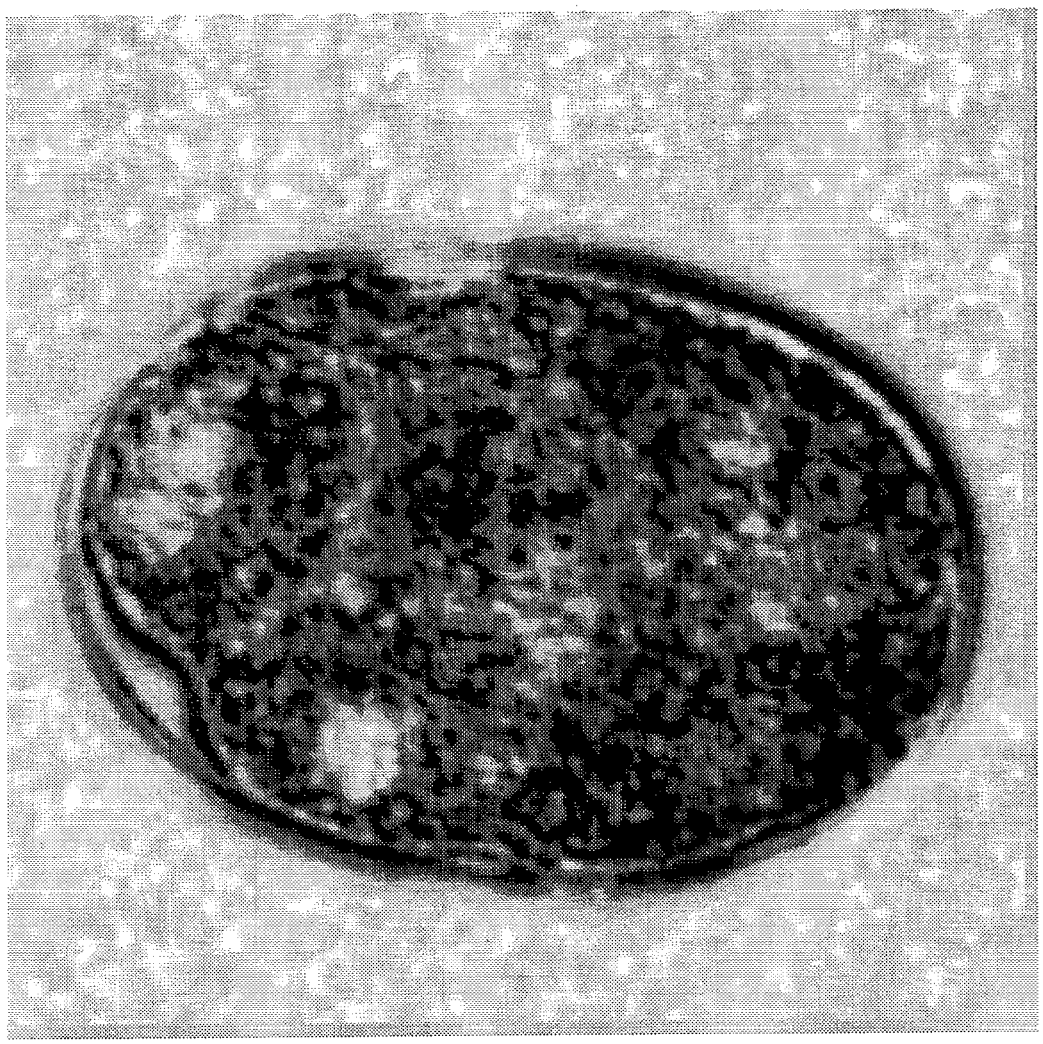
FIG. 17 is the image after processing using the entropy filter.
Figure 18:
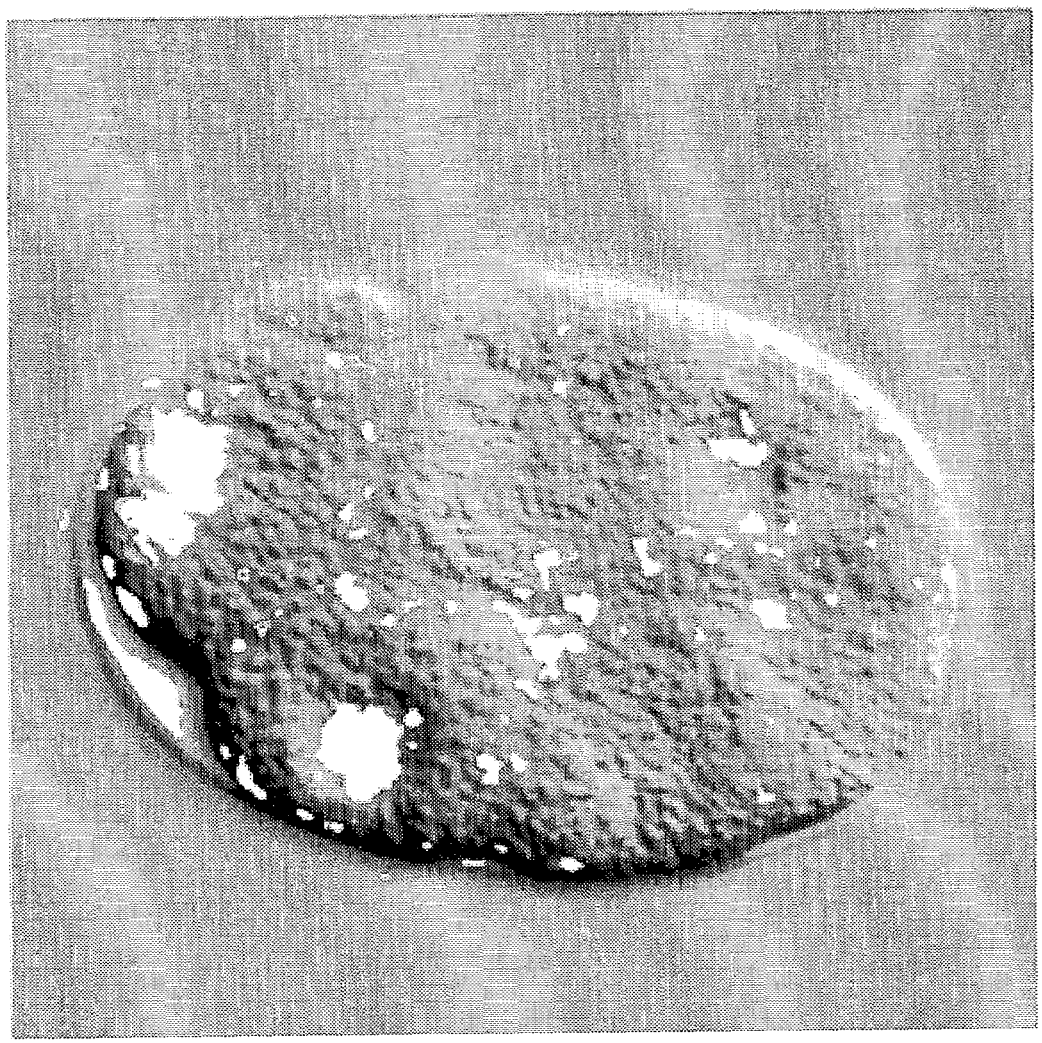
FIG. 18 is a product of superimposing the resultant image, which has been processed by the entropy filter followed by threshold processing, on the microscopic image.

The operation involving the calculation of entropy of a small partition scanning the original image makes efficient extraction of the position of the nucleus possible. The entropy window size depends on the kind of microscope and magnification used. A good result was obtained by scanning the image area window of 6[pixels]×6 [pixels] to 20 [pixels]×20 [pixels], (preferably 10 [pixels]×10 [pixels] or 12 [pixels]×12 [pixels]). In this case, the pixel of the nucleus area ranges according to factors such as cell division from about 1000 pixels to 10000 pixels. FIG. 17 is the image (filtering image) of the cell after processing using the entropy filter. FIG. 18 is the product of superimposing the resultant image, which has been processed by the entropy filter followed by threshold processing, on the microscopic image.

Partitioning the image by a small window and scanning the image calculating entropy facilitates the extraction of smooth portions from the image. The threshold processing of the filtered image yielded by the entropy filter allows good extraction of the smooth portion from the image. In the present specification, "smooth" is defined as the difference in pixel values being relatively small, in other words, an intensity value of the pixel is relatively even. In contrast, "not smooth" is defined as the difference in pixel values being relatively large, in other words, an intensity value of the pixel is relatively uneven. The intensity value in a gray scale image is the value representing monochromic intensity. The intensity value in a color image is the value representing each intensity of R, G, and B. Whether "The difference in pixel values is small or large" in the color image is determined according to the proviso that, the closer the combination of R, G, and B, the smaller the difference, while the more dissimilar the combination of R, G, and B, the larger the difference.

[FFT Filter]

For the image area to be measured for characteristics, a 2D FFT power spectrum (fast Fourier transform power spectrum) is calculated and the nucleus area is detected using the characteristics of a low frequency and a high frequency area. A normal Fourier transform can be applied. The result of an output of the filter is used following binarization.

INDUSTRIAL APPLICABILITY

In fields of pharmacy, medical care, agriculture, and food, the present invention can be applied to product development using effective genomic information.

The invention claimed is:

1. A method for constructing a cell lineage comprising the steps of:
    (a) obtaining a plurality of 2D images different in focal plane and time by taking a plurality of 2D images changing the focal plane and taking a plurality of 2D images in a time series for a cell constituting the subject of observation;
    (b) extracting a nucleus area by carrying out image processing for individual 2D images;
    (c) unifying the nucleus area extracted from the individual 2D images, which is derived from an identical nucleus; and
    (d) constructing the cell lineage from a time and a position, where the nucleus area emerges and disappears in the image, in the unified nucleus area.

2. The method as claimed in claim 1, wherein the image is taken by a DIC microscope.

3. The method as claimed in claim 1, wherein the step for extracting comprises image processing that utilizes the difference in the brightness of the image between the nucleus and the remaining part of the cell.

4. The method as claimed in claim 3, wherein the step for extracting comprises detecting an area where the brightness variation in the image is poor as a nucleus.

5. The method as claimed in claim 4, wherein said detecting comprises one or more filters selected from the group consisting of a Kirsh filter, Prewitt filter, and FFT filter.

6. The method as claimed in claim 1, wherein the step for extracting comprises extracting a part where the intensity is large in a wide range along the incident angle of light as a nucleus.

7. The method as claimed in claim 6, the extracting comprises a step for taking a difference in a sum of intensity value of a predetermined top and bottom pixel along a seeming direction of light.

8. The method as claimed in claim 7, wherein the method comprises the steps of extracting a cell boundary and extracting an embryo area and wherein the result obtained by the method in claim 7 may be corrected based on the result obtained by the method in claim 7.

9. The method as claimed in claim 1, wherein the step for extracting comprises a plurality of different nucleus detecting algorithms and wherein an area recognized as a nucleus by any one of the algorithms is determined as the nucleus area in the image processing system as a whole.

10. The method as claimed in claim 1, wherein the extracting comprises the steps of: partitioning the cell image by a small window; scanning the image by calculating entropy of the window; and extracting the nucleus area from the image.

11. The method as claimed in claim 1, wherein the unifying comprises the steps of: unifying nucleus areas, which are derived from identical nucleus, contained in an image group on an identical focal plane; unifying nucleus areas, which are derived from identical nuclei, contained in an image group at an identical time; and further unifying the nucleus areas obtained by said two steps.

12. The method as claimed in claim 11, wherein the step for unifying the nucleus areas obtained by said two steps comprises unifying the nucleus areas in the case where there exists a combination of unified nucleus areas, which have a common nucleus area, between the nucleus areas unified in both the time series and the focal direction, these are regarded as a unified nucleus area derived from an identical nucleus, and are further unified.

13. The method as claimed in claim 1, wherein the constructing comprises detecting a parent cell and a daughter cell after division of the parent cell by obtaining a 4D distance between the nucleus areas.

14. A method for constructing a cell lineage comprising the steps of:
(a) obtaining a plurality of 2D images different in focal plane and a time by taking a plurality of the 2D images by changing the focal plane and taking a plurality of the 2D images in a time series for a cell constituting the subject of observation;
(b) extracting a nucleus area by carrying out image processing for individual 2D images;
(c) unifying the nucleus area, which is derived from the identical nucleus, from the nucleus area extracted from the individual 2D images;
(d) constructing the cell lineage from a time and a position, where the nucleus area emerges and disappears in the image, in the unified nucleus area; and wherein
(e) said step (b) comprises the steps of: extracting the area to become a candidate of the nucleus; designating a presumable nucleus area by a trial operation of cell lineage preparation; and extracting the nucleus area by feedback of the presumable area to the nucleus candidate area.

15. The method as claimed in claim 14, wherein the trial operation of cell lineage preparation includes at least one of unifying nucleus areas in an identical time and an identical focal plane, unifying 4D nucleus areas, and preparing the cell lineage, thereby allowing feedback of the designation of the presumable nucleus area by the trial operation.

16. The method as claimed in claim 15, wherein the feedback from unifying nucleus areas in an identical time and an identical focal plane comprises the steps of:
choosing the nucleus area; unifying the nucleus areas in the identical time and the identical focal plane; designating the nucleus candidate area; and feeding the result of the designation of the presumable nucleus area to the step for choosing the nucleus area.

17. The method as claimed in claim 15, wherein the feedback from unifying 4D nucleus areas comprises the steps of: choosing a 3D nucleus area; unifying 4D.

18. The method as claimed in claim 15, wherein the feedback from preparing the cell lineage comprises the steps of: choosing a 4D nucleus area; preparing the cell lineage; designating the nucleus candidate area; and feeding the result of the designation of the presumable nucleus area to the step for choosing the nucleus area.

19. The method as claimed in claim 14, wherein said nucleus candidate area is given with a nucleus score and the nucleus area is extracted by comparing the nucleus score and a predetermined specified value, and wherein the nucleus score is to be changed by the feedback of the presumable nucleus area.

20. The method as claimed in claim 14, wherein the step for extracting the nucleus candidate area comprises the steps of: image-processing the image using the difference in the brightness of the image regarding the nucleus and the remaining part of the cell;
designating the nucleus candidate area; and giving the nucleus score to the nucleus candidate area.

21. The method as claimed in claim 20, wherein the extracting the nucleus candidate area comprises designating the nucleus area by binarizing the result obtained by the image processing using a predetermined threshold and the nucleus score is given to the designated area.

22. The method as claimed in claim 20, wherein the extracting the nucleus candidate area comprising extracting polar areas in a direction of black in the resultant image obtained after the image processing accompanying a score as the nucleus candidate area. nucleus areas; designating the nucleus candidate area; and feeding the result of the designation of the presumable nucleus area to the step for choosing the nucleus area.

* * * * *

UNITED STATES PATENT AND TRADEMARK OFFICE
CERTIFICATE OF CORRECTION

| | |
|---|---|
| PATENT NO. | : 7,110,584 B2 |
| APPLICATION NO. | : 10/182429 |
| DATED | : September 19, 2006 |
| INVENTOR(S) | : S. Onami et al. |

It is certified that error appears in the above-identified patent and that said Letters Patent is hereby corrected as shown below:

COLUMN           LINE

21                   37              "identical nucleus," should read --identical nuclei,--
(Claim 11,           line 3)

22                   29              after "unifying 4D" insert --, nucleus areas; designating
(Claim 17,           line 3)         the nucleus candidate area; and feeding the result of the
                                     designation of the presumable nucleus area to the step
                                     for choosing the nucleus area--

22                   60              after "candidate area", delete ", nucleus areas;
(Claim 22,           line 5)         designating the nucleus candidate area; and feeding the
                                     result of the designation of the presumable nucleus area
                                     to the step for choosing the nucleus area"

Signed and Sealed this

Sixth Day of May, 2008

JON W. DUDAS
*Director of the United States Patent and Trademark Office*